US010928325B1

(12) United States Patent
McCord et al.

(10) Patent No.: US 10,928,325 B1
(45) Date of Patent: Feb. 23, 2021

(54) URINE TEST SYSTEM WITH NUTRITIONAL RECOMMENDATIONS

(71) Applicant: VESSEL HEALTH, INC., San Diego, CA (US)

(72) Inventors: Matthew McCord, San Diego, CA (US); Jon Carder, San Diego, CA (US)

(73) Assignee: VESSEL HEALTH, INC., San Diego, CA (US)

( * ) Notice: Subject to any disclaimer, the term of this patent is extended or adjusted under 35 U.S.C. 154(b) by 0 days.

(21) Appl. No.: 16/870,730

(22) Filed: May 8, 2020

Related U.S. Application Data

(63) Continuation-in-part of application No. 16/828,967, filed on Mar. 25, 2020.

(51) Int. Cl.
*G01N 21/78* (2006.01)
*G06T 7/90* (2017.01)
*H04N 1/60* (2006.01)
*G06T 7/00* (2017.01)

(52) U.S. Cl.
CPC .......... *G01N 21/78* (2013.01); *G06T 7/0012* (2013.01); *G06T 7/90* (2017.01); *H04N 1/6077* (2013.01); *G01N 2800/02* (2013.01); *G06T 2207/10024* (2013.01); *G06T 2207/30004* (2013.01)

(58) Field of Classification Search
CPC ...... G01N 21/78; G01N 2800/02; G06T 7/90; G06T 7/0012; G06T 2207/30004; G06T 2207/10024; H04N 1/6077
See application file for complete search history.

(56) References Cited

U.S. PATENT DOCUMENTS 9,311,520 B2   4/2016   Burg et al.

OTHER PUBLICATIONS

Compound Solutions, Inc. Website. <https://connpoundsolutions.com/micronutrients-in-the-ketogenic-diet/> downloaded by the examiner on Jul. 2, 2020, published Jan. 16, 2018. (Year: 2018).*

* cited by examiner

*Primary Examiner* — Christopher Adam Hixson
(74) *Attorney, Agent, or Firm* — Arc IP Law, PC; Joseph J. Mayo

(57) ABSTRACT

System that makes nutritional recommendations based on results of a home urine test. A user may apply a urine sample to a card containing multiple tests, and capture an image of the card using a phone; an analysis system executing on the phone or in the cloud may analyze the image and determine test results. The test card and analysis system may compensate for variability in lighting conditions and time of exposure to the urine sample. Based on test results, the system may recommend consumption of specific quantities of nutrients, such as vitamins, minerals, and foods. It may also recommend consumption of water or electrolytes based on measured hydration, and stress reduction techniques or sleep based on measured cortisol. Recommendations may be customized based on factors such as the user's characteristics (gender, weight, etc.), predicted absorption of nutrients from food or supplements, and the user's dietary preferences or restrictions.

30 Claims, 19 Drawing Sheets

FIG. 12

Vitamin C Recommended Daily Allowance, mg/day

Male — 1104a

| Age | RDA |
|---|---|
| 1-3 | 15 |
| 4-8 | 25 |
| 9-13 | 45 |
| 14-18 | 75 |
| 19-30 | 90 |
| 31-50 | 90 |

1201

Female — 1104b

| Age | Standard RDA | Pregnant RDA | Lactating RDA |
|---|---|---|---|
| 1-3 | 15 | | |
| 4-8 | 25 | | |
| 9-13 | 45 | | |
| 14-18 | 65 | 80 | 115 |
| 19-30 | 75 | 85 | 120 |
| 31-50 | 75 | 85 | 120 |

URINE TEST SYSTEM WITH NUTRITIONAL RECOMMENDATIONS

This application is a continuation-in-part of U.S. Utility patent application Ser. No. 16/828,967, filed on 25 Mar. 2020, the specification of which is hereby incorporated herein by reference.

BACKGROUND OF THE INVENTION

Field of the Invention

One or more embodiments of the invention are related to the field of biochemical analysis of a body fluid, such as a urine or saliva sample. More particularly, but not by way of limitation, one or more embodiments of the invention enable a system that collects and analyzes a urine sample for multiple analytes, and that makes nutritional recommendations based on the test results.

Description of the Related Art

Home urine testing systems such as dipsticks are available for certain tests, such as pregnancy tests. To be usable in a home environment by a consumer, a urine testing system must provide results that are easily interpreted by the user. This requirement has generally limited the types and complexity of urine tests that may be used in a home environment. For example, large panels of urine tests on a single test card cannot be easily interpreted by a user. In addition, certain types of tests indicate the presence or quantity of an analyte via subtle color or shade changes that a user may not be able to judge reliably.

To address these limitations, some systems have recently emerged that use smartphones to capture an image of a urine test card and to analyze the image to generate test results. A challenge with these systems is that the conditions under which the images are captured are not well controlled in a home environment, unlike in a laboratory. Key uncontrolled variables include lighting conditions and the time elapsed between exposing a test card to urine and capturing an image of the card. An illustrative system that uses a smartphone to analyze images of a urine test card is described in U.S. Pat. No. 9,311,520, "Method and apparatus for performing and quantifying color changes induced by specific concentrations of biological analytes in an automatically calibrated environment." This patent describes a color correction process that attempts to adjust for variable lighting conditions; however, the method described in this patent assumes uniform lighting across the test card. In addition, this system does not address variation in the timing of image captures; instead it presumes that a user may be prompted to capture an image at an appropriate time. These limitations of this system and similar systems may reduce the accuracy of test results from urine tests in a home environment.

One potential application of home urine testing is nutritional counseling. Currently to obtain nutritional counseling, a consumer typically visits a nutritionist. The nutritionist may perform an extensive interview on the consumer's dietary habits, and may perform certain tests as part of an assessment. The nutritionist may then develop a customized plan for the consumer. This process is time-consuming, expensive, and infrequent. There are no known systems that provide automated nutritional recommendations based on in-home testing, and that adjust these recommendations continuously as test results change on a daily basis.

For at least the limitations described above there is a need for a urine test system with nutritional recommendations.

BRIEF SUMMARY OF THE INVENTION

One or more embodiments described in the specification are related to a urine test system with nutritional recommendations. One or more embodiments may for example enable home urine testing, and may compensate for variability in lighting conditions and time of exposure to urine that are more likely to occur in a home environment. One or more embodiments may generate nutritional recommendations based on urine test results.

One or more embodiments of the invention include a test card and a test analyzer. The test card, which is exposed to a urine sample, may contain multiple test regions to test for multiple factors in the urine. Each test region may contain reagents that react with one or more substances in the urine sample, and that change appearance based on the presence or quantity of those substances. The test card may contain one or more time indicators that change appearance based on how long they are exposed to the urine sample. It may also contain multiple fiducial markers that may be used for lighting and color correction. Each fiducial marker may have a reference color that is measured in or defined with respect to a reference lighting condition.

The test analyzer may include a stored program or programs that execute on one or more processors. The user of a test card may capture an image of the card after exposing it to the urine sample, and after waiting for the reactions in the test regions to occur. This image may then be analyzed by the analysis program. The analysis program may extract from the image the appearance of the fiducial markers, the time indicator(s), and the test regions. It may generate a color adjustment that transforms the observed colors of the fiducial markers into their reference colors; this adjustment may therefore compensate for the variability of the lighting conditions under which the test card image is captured. The color adjustment may be applied to the appearance of the test regions, and potentially as well to the appearance of the time indicator(s). The analysis program may analyze the adjusted appearance of the time indicator(s) to determine how long the test card has been exposed to the urine sample.

Finally, the test program may calculate the presence or quantity of the substances of interest in each test region based on the adjusted appearance of the test region and on the calculated elapsed time of exposure to the urine sample.

In one or more embodiments, the color adjustment may be a function of the colors in the image of a region and of the position in the test card of the region. By including position as an input into the color adjustment function, the analysis system may be able to compensate for variability in lighting across the card.

One or more embodiments may use a linear color adjustment function, which may for example be a sum of a color factor, a position factor, and an offset. The color factor may be calculated as a product of a matrix and the color of a region in the image (as a 3 channel vector, for example). The position factor may be calculated as a product of a matrix and the position of the region in the image. The offset may be a vector added to the result for all regions.

In one or more embodiments, fiducial markers may include corner fiducials at the corners of a portion of the card containing the test regions. The reference colors of the corner fiducials may be identical. The fiducial markers may also contain multiple color fiducial markers. For example, in one or more embodiments there may be at least 3 color fiducial markers of different reference colors. One or more embodiments may have 9 or more color fiducial markers of different reference colors. One or more embodiments may have 12 or more color fiducial markers of different reference colors.

The linear color adjustment function may be calculated for example as a linear regression having inputs of the observed colors and positions of the corner fiducial and color fiducial markers, and having outputs of the reference colors of the fiducial markers.

In one or more embodiments the analysis system may analyze the image of the test card to identify certain lighting anomalies, which may for example make the image unusable; it may inform the user that the image is unusable, and may prompt for another image. For example, one or more embodiments may analyze the image for excessive glare. Glare may be detected for example if an area of the image has a color value that is very different from the color value of the area under the reference lighting condition. Glare may also or alternatively be detected if an area of the image has a color value that is very different from adjacent areas that should have similar values under the reference lighting condition.

Lighting anomalies may include shadows. One or more embodiments may analyze the image for shadows by comparing the color values of the corner fiducial markers; if these values are very different, the system may determine that part of the card is in shadow and generate a message that the image is unusable. For example, if the maximum value of the corner fiducials on a specific color channel (such as lightness) less the minimum value on that color channel exceeds a threshold, a shadow may be detected.

One or more embodiments of the test card may contain two time indicators. The elapsed time estimates from each of the time indicators may be compared; if they vary significantly then the system may determine that the test results are not valid. Elapsed time associated with a time indicator may be determined by comparing the adjusted appearance of the time indicator to a time indicator calibration sequence, which exposes a reference time indicator to urine for a sequence of known times and records the reference appearance at each time. Time indicators may be for example lateral flow assays with only non-human antibodies, so that human substances in the urine do not affect the appearance of the time indicators.

After adjusting test region appearances for lighting, and calculating exposure time, one or more embodiments may determine test results by comparing observed colors of test regions to a calibration curve for that type of test region. A calibration curve may be generated for example by exposing the reagents of a test region to different quantities of the substances being tested for, and observing the appearance of the test region under the reference lighting condition. Calibration curves may be calculated for different exposure times. The analysis system may obtain the calibration curve that corresponds to the elapsed time of exposure as measured for example by the time indicator(s). The test result indicating the presence or quantity of the substances may be determined based on the closest point on the calibration curve to the adjusted appearance of a test region.

In one or more embodiments the test card may contain an identifying code, such as for example a QR code. This code may indicate or be linked to information describing the test regions on the card. It may also indicate the manufacturing batch of the test card.

In one or more embodiments the test card may contain four or more lateral flow assays and fifteen or more colorimetric tests.

One or more embodiments may include a computer that specifically calculates a recommended consumption level for one or more substances measured in the urine test. The recommended consumption may be based on the measured level in the urine and on a suggested range for the level for the person who is tested. Recommended consumption may also be based on one or more characteristics of the person, such as for example one or more of gender, weight, height, body mass index, age, pregnancy status, allergies, medications, medical conditions, ethnicity, genome, microbiome, dietary restrictions, lifestyle, activity level, mental health, and personal goals. These characteristics may also affect the suggest range for the urine level for the person. In one or more embodiments, the measured level or reported level of a substance in the urine may be selected from a set of discrete values; each value may correspond for example to a range of substance concentrations. Similarly, in one or more embodiments the recommended consumption levels may be selected from a set of discrete values.

Recommended consumption of a substance may include a recommended consumption from food, and a recommended consumption from supplements. These values may differ based on different absorption of the substance from food and supplements. The recommended food consumption of the substance may be based on the measured level in urine, the suggested range for this level, and a food multiplier that reflects the effectiveness of the person obtaining the substance from food. Similarly the recommended supplement consumption of the substance may be based on the measured level in urine, the suggested range for this level, and a supplement multiplier that reflects the effectiveness of the person obtaining the substance from supplements. Calculation of recommended consumption levels may be based on a substance level score that is 100% when the level in the urine is within the suggested range, and that may fall below 100% when the measured level is below the suggested range. A deviation score may be calculated as 100% less the substance level score. Recommended food consumption may be calculated as the recommended daily allowance for the substance plus the product of the deviation score, the recommended daily allowance, and the food multiplier factor. Recommended supplement consumption may be calculated as the product of the deviation score, the recommended daily allowance, and the supplement multiplier factor. In one or more embodiments the calculated recommended consumption levels may be further adjusted based on characteristics of the person, such as gender, weight, height, body mass index, age, pregnancy status, allergies, medications, medical conditions, ethnicity, genome, microbiome, dietary restrictions, lifestyle, activity level, mental health, and personal goals.

In one or more embodiments the computer may also recommend one or more foods and quantities of these foods, where the foods contain the recommended food consumption of the substance. Food recommendations may also be based on dietary preferences or restrictions of the person. In one or more embodiments the system may measure a person's hydration level, based for example on the specific gravity of the urine sample. Based on the hydration level, the system may recommend changes in fluid or electrolyte consumption.

In one or more embodiments, the system may recommend lifestyle changes in addition to or instead of recommending changes in consumption of nutrients. These lifestyle changes may include for example changes to activity levels. Lifestyle recommendations may for example be based on measurements of cortisol in the urine sample, which may be correlated for example with stress levels. If cortisol levels are outside normal ranges or are trending unfavorably, the system may recommend adding a certain number of minutes of activity per day, where the amount of added activity may be based on how far the cortisol level deviates from a normal range. The system may propose one or more activities, such as for example walking, exercise, yoga, meditation, or sleep. One or more embodiments may measure other substances that are correlated with lifestyle, such as melatonin, and may make lifestyle change recommendations accordingly.

BRIEF DESCRIPTION OF THE DRAWINGS

The above and other aspects, features and advantages of the invention will be more apparent from the following more particular description thereof, presented in conjunction with the following drawings wherein:

FIG. 12 shows recommended daily allowances for Vitamin C—an illustrative nutrient that may be measured by a urine test card.

DETAILED DESCRIPTION OF THE INVENTION

A urine test system with nutritional recommendations will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1A:
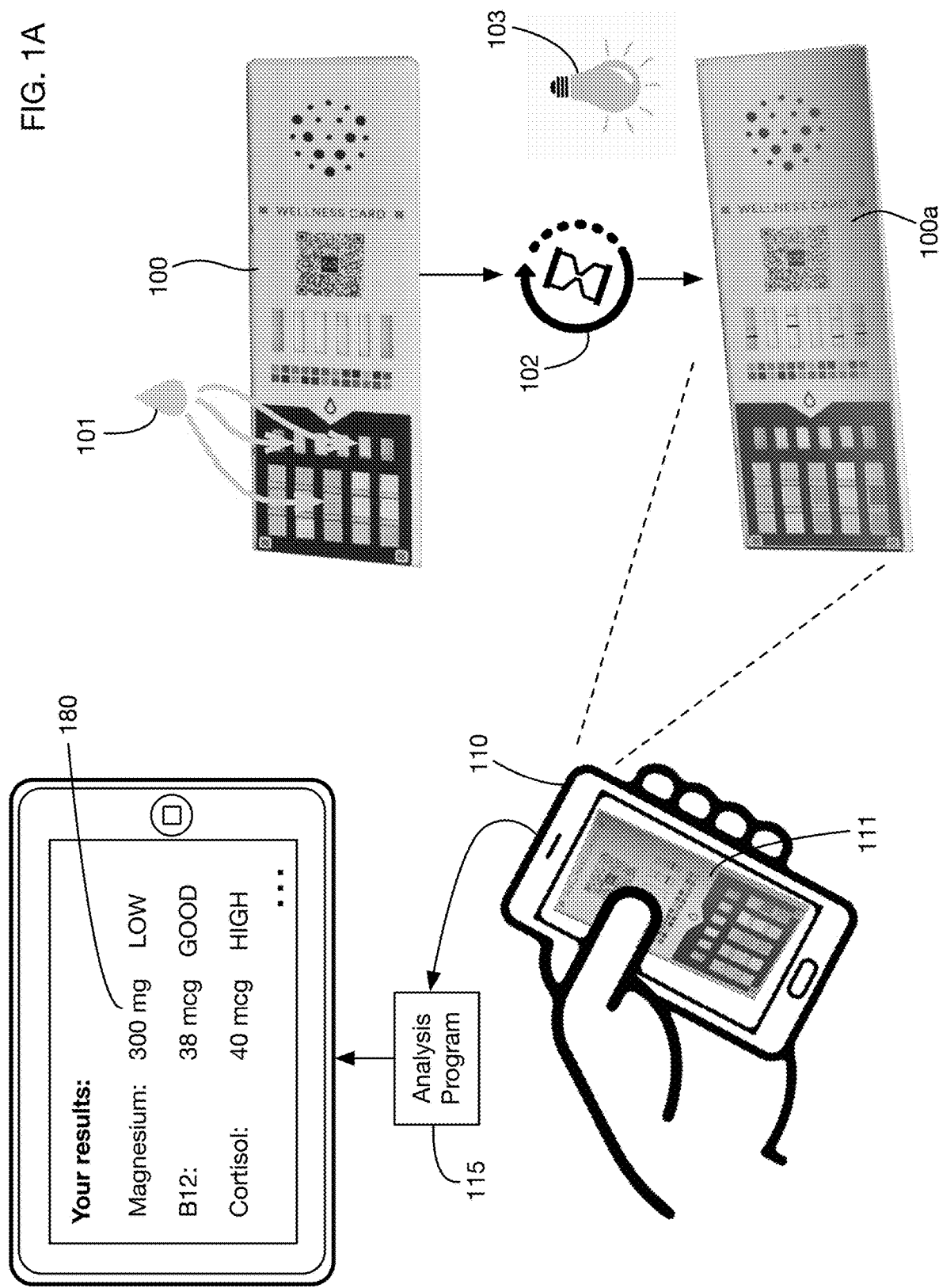
FIG. 1A shows capture of an image of an illustrative urine test card under unknown lighting and timing conditions, and analysis of this image to determine test results.

One or more embodiments of the invention may include a test card that contains one or more urine tests, and a test analyzer system that determines test results by analyzing an image of the test card after it has been exposed to a urine sample. FIG. 1A shows an illustrative test card 100 prior to exposure to a urine sample. The test card may contain various types of tests with reagents that react to specific analytes in a urine sample. The test regions on the test card may include for example colorimetric tests and lateral flow assays. The test card may also contain color fiducials for color correction, and one or more time indicators for timing correction, as described in detail below. FIG. 1A shows an illustrative use of the test card and test analyzer system. A user exposes test card 100 to a urine sample 101 (for example by dipping the end of the card into the sample, or by urinating directly on the card). The user then waits a period of time 102 for the reagents in each test region of the card to react with the urine sample, and then captures an image (or images) 111 of the test card 100a (after exposure). This image may be captured for example using a smartphone 110 or similar device. Device 110 may be for example, without limitation, a smart phone, a smart watch, a tablet, a laptop computer, a notebook computer, a desktop computer, smart glasses, a virtual reality headset, a specialized chemistry reader, or any combination of these devices. In one or more embodiments a user may capture an image 111 using any camera or cameras, and then upload this image to another system or systems for analysis.

Because the test card 100 may be used in a home environment, instead of a laboratory, the lighting conditions 103 under which image 111 is captured may be variable and uncontrolled. This variability presents a specific challenge for the analysis of the test image; solutions to this challenge are described below. Another challenge is that the amount of time 102 that elapses between exposure of test card 100 to urine sample 101 and the capture of image 111 may be variable and uncontrolled. Even if the system prompts the user to capture an image after a specific amount of time, there is variation on when the user starts the timer for this prompt and how long the card was exposed to urine before beginning this process. User reaction times and other delays may affect the amount of time 102. Solutions to the challenge of timing variability are also described below.

Image 111 is then analyzed by a test analyzer that includes an analysis program 115, which determines the results of the tests integrated into test card 100. These results 180 may be displayed for example on device 110 or on any other device. The analysis program may be stored on and may execute on the image capture device 110 (such as a smartphone), or on any other processor or combination of processors. For example, some or all of the analysis may be performed by programs executing on servers that receive the image 111 or data from the image via an internet connection to device 110. In one or more embodiments some of the image analysis may be performed locally on device 110, and some may be performed remotely (for example on cloud-connected servers). In one or more embodiments all of the image analysis may be performed locally on device 110. In one or more embodiments all of the image analysis may be performed remotely (for example on cloud-connected servers).

Figure 1B:
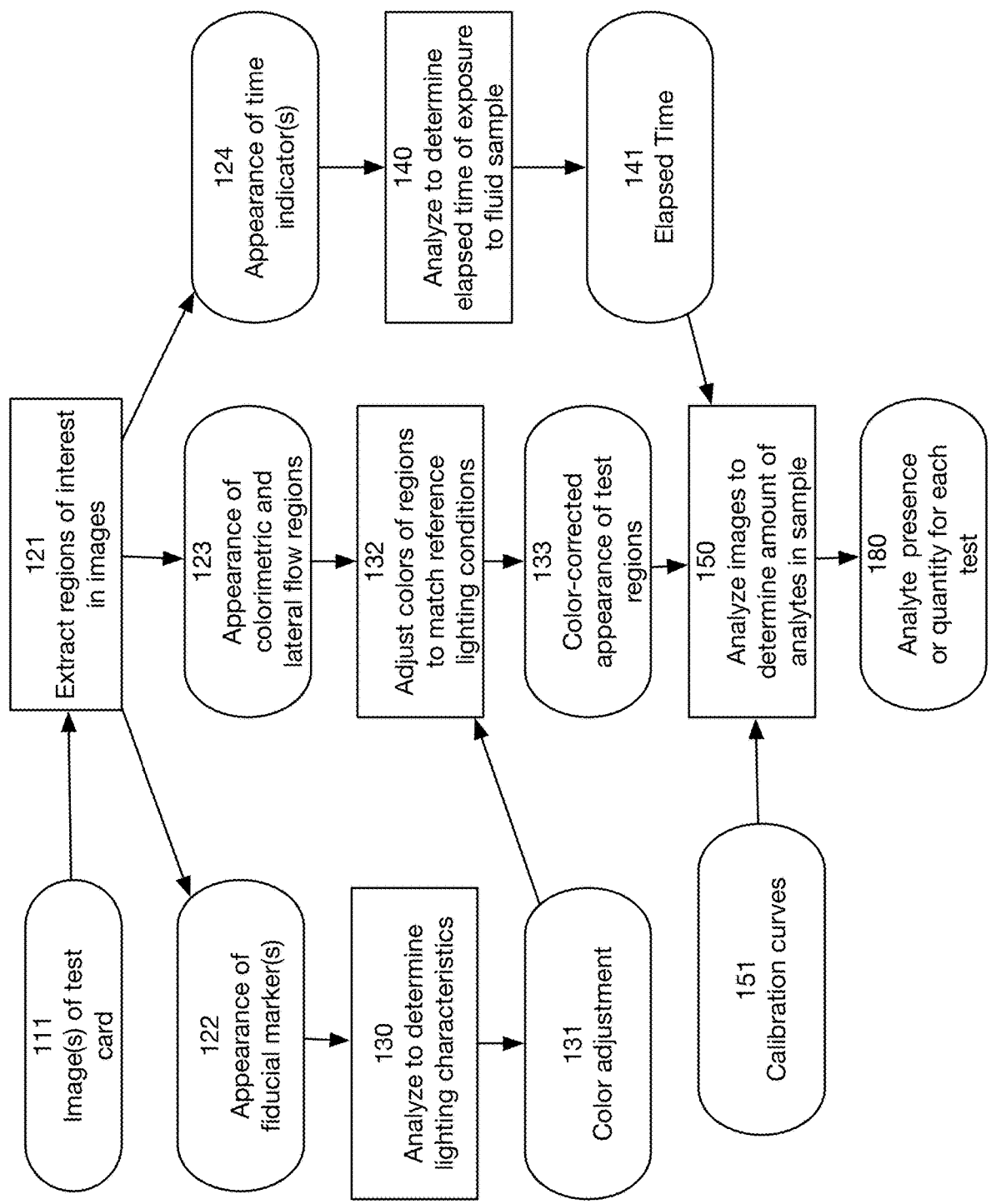
FIG. 1B shows a flowchart of processing steps performed by an illustrative embodiment of the invention to adjust for lighting and timing conditions.

FIG. 1B shows illustrative processing steps that may be performed in one or more embodiments of analysis program 115. As described above, these steps may be performed by a stored program or programs executing on any processor or combination of processors. One or more images 111 of the test card may be input into step 121, which extracts regions of interest from the image(s). Extraction 121 may include geometric transformations on the image to correct for angular distortion (for example if the user holds the card at an angle relative to the camera) or for camera distortions. Outputs of extraction step 121 may include for example appearance of fiducial markers 122, appearance of test regions on the test card 123 (such as lateral flow assay regions and colorimetric test regions), and appearance of time indicator(s) 124. Other regions of interest that may be extracted may include regions containing identifying information on the card such as a bar code or QR code.

Appearance of fiducial markers 122 may then be analyzed in step 130 to determine the lighting conditions under which the image 111 was captured. This analysis results in a color adjustment function or procedure 131, which may for example transform observed colors in regions of the test card to colors that would be observed under reference lighting conditions. This transformation may be performed in step 132, which adjusts the appearance 123 of the test regions of the card, resulting in color-corrected appearances 133 of these test regions.

Appearance of time indicator(s) 124 may be analyzed in step 140 to determine the elapsed time 141 between exposure of the test card to the urine sample and the capture of the test image(s) 111.

The color-corrected appearances 133 and the elapsed time 141 may then be used in step 150 to determine the presence or amounts of analytes in the urine sample. This step 150 may use calibration curves 151 that relate the analyte amounts to the expected appearance of each region as a function of elapsed time. The output of step 150 is the test results 180 with the presence or quantity of each analyte.

Figure 2:
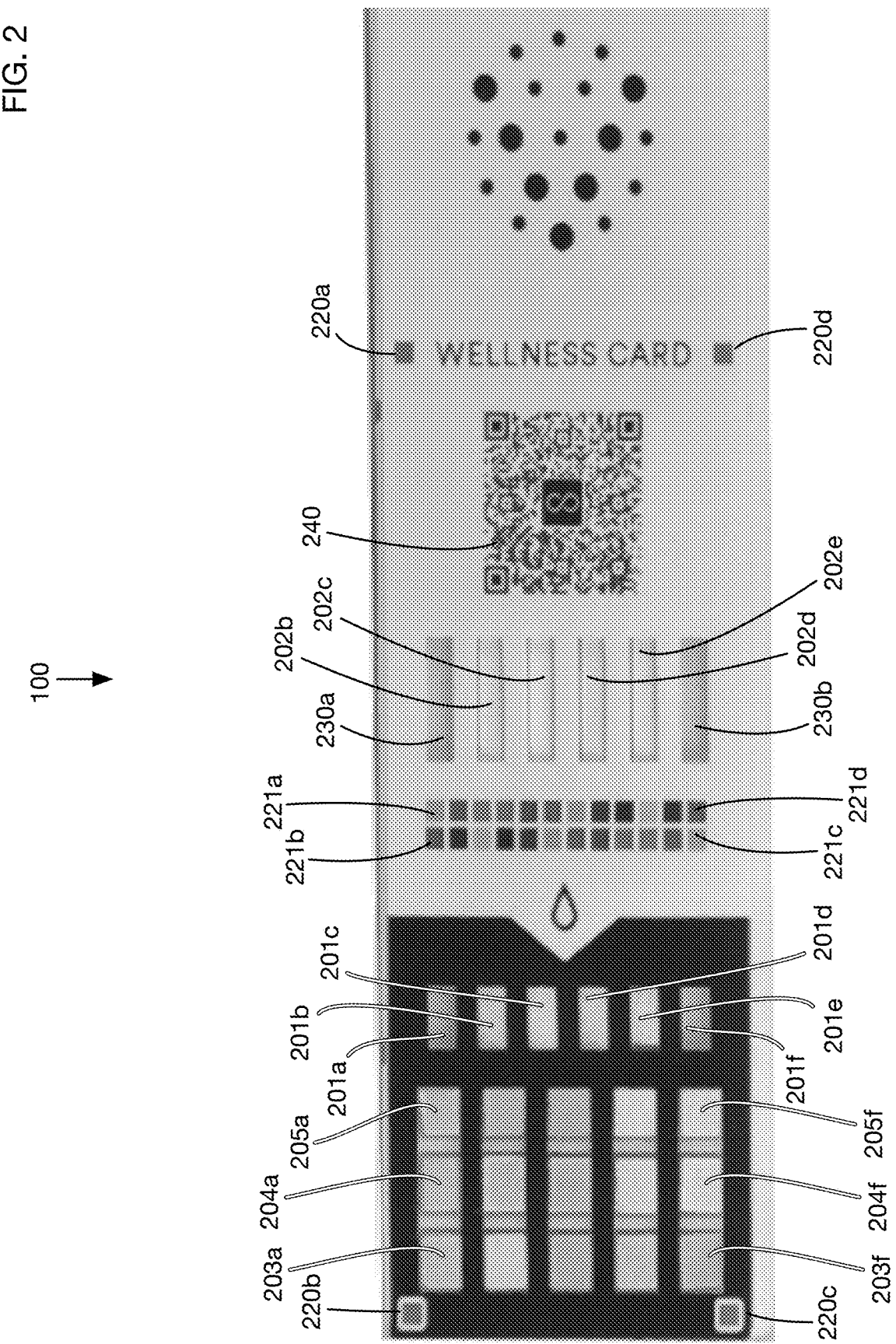
FIG. 2 shows an illustrative urine test card that integrates lateral flow tests, colorimetric tests, color fiducials for color correction, and timing strips for timing correction.

FIG. 2 shows an image of an illustrative test card 100 that may be used in one or more embodiments of the invention. This illustrative card has 4 lateral flow assay test regions 202b, 202c, 202d, and 202e, and it has 15 colorimetric test regions such as regions 203a, 204a, and 205a shown at the top and regions 203f, 204f, and 205f shown at the bottom. One or more embodiments may have any type of test regions, including but not limited to lateral flow and colorimetric tests. Each test region may contain reagents or combinations of reagents that react with specific elements that may be present in a urine sample to generate a visible change in the appearance of the test region.

Test regions may be exposed directly to a urine sample, or they may receive the urine sample for example from another pad or chamber to which urine is added. For example, urine may be wicked along a pad from one point in the test card to another. In the illustrative embodiment 100 shown in FIG. 2, the colorimetric test regions (203a through 205f) are exposed directly to the urine sample. The lateral flow assay regions 202b through 202e receive urine from corresponding pads 201b, 201c, 201d, and 201e. These pads have a small portion that is exposed through the cover of the test card, and the remainder of the pads form a wicking channel that carries urine to the corresponding lateral flow assays. One or more embodiments may route urine fluid on the test card using any desired method, such as wicking pads, capillaries, or microfluidic channels of any type.

Illustrative test card 100 contains several fiducial markers that may be used to adjust the appearance of card images for varying lighting conditions. The fiducial markers may also be used in one or more embodiments to correct the geometry of captured images since the markers may be in known positions and orientations on the card. Card 100 has four corner fiducial markers 220a, 220b, 220c, and 220d. The test regions are contained in the area bounded by these corner fiducial markers. A benefit of placing fiducial markers at the boundary of the test regions is that variation in lighting conditions across the card may be more easily detected. In this embodiment, the corner fiducial markers 220a through 220d are all of the same color, which is a neutral gray. In one or more embodiments the corner fiducial markers may be of any color or colors, and of any size and shape.

Test card 100 also contains two rows of color fiducial markers such as 221a and 221b at the top of the image in FIG. 2, and 221c and 221d at the bottom of the image in FIG. 2. In this illustrative embodiment there are 24 color fiducial markers. These are of various colors, with some repetition of colors in the embodiment shown in FIG. 2. In one or more embodiments, color fiducial markers may be located anywhere on test card 100; they may be of any colors, sizes, and shapes. One or more embodiments may have any number of color fiducial markers and any number of distinct colors for these markers. For example, in one or more embodiments there may be 3 or more color fiducial markers with 3 or more distinct colors. In one or more embodiments there may be 9 or more color fiducial markers with 9 or more distinct colors. In one or more embodiments there may be 12 or more color fiducial markers with 12 or more distinct colors.

Test card 100 has two time indicators 230a and 230b. In this embodiment, these time indicators are specialized lateral flow assays that change appearance as a function of the time of exposure to a urine sample, regardless of the contents of the sample. These time indicators 230a and 230b receive urine from pads 201a and 201f, respectively. A potential benefit of having two (or more) time indicators is that the redundancy may be used to validate the exposure time estimates. For example, if the two time indicators 230a and 230b indicate substantially different exposure times, the results from the test card may be questionable. Placing the two time indicators on opposite edges of the card also helps assure that urine exposure and flow is similar throughout the card.

Test card 100 also has a QR code 240 which may uniquely identify the card or the type of card. This code may contain or may be linked for example to information on the tests on the card, to the manufacturing date and batch, or to any other information used for analysis or quality assurance.

Figure 3B:
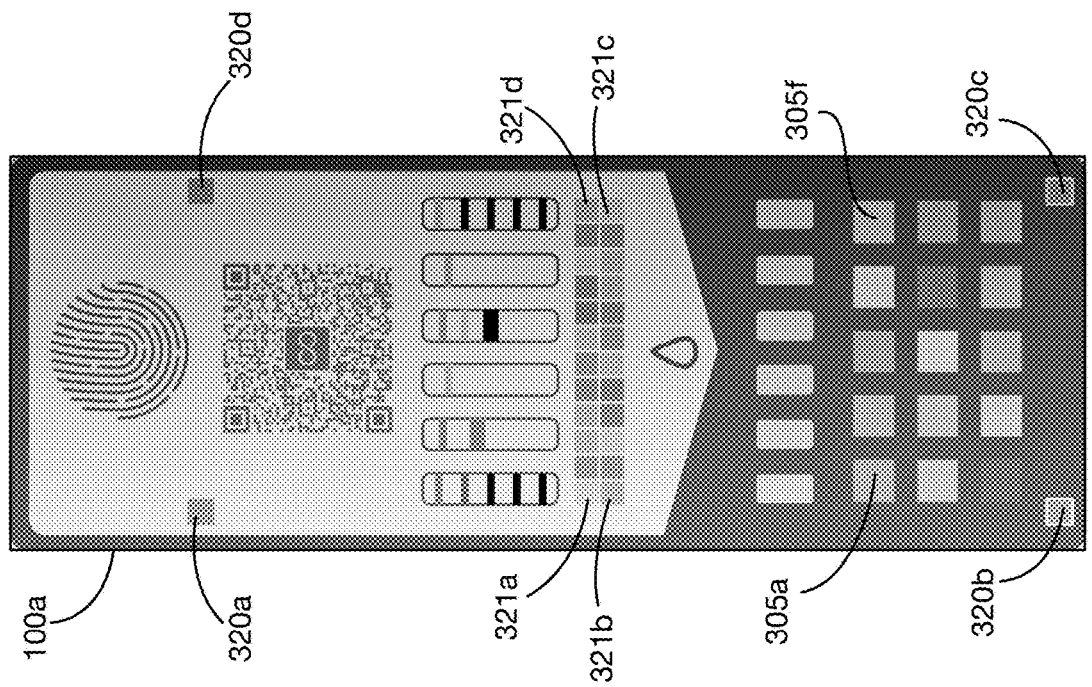
FIG. 3B shows the test card of FIG. 3A after exposure to urine, imaged under lighting conditions that differ from the reference conditions.
Figure 3A:
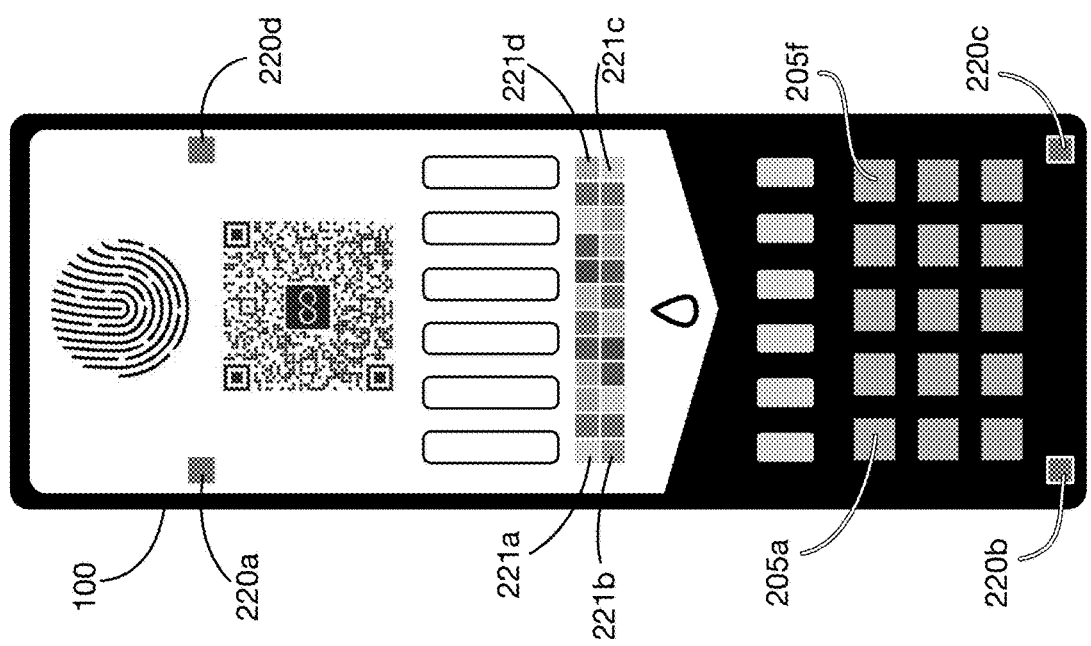
FIG. 3A shows a diagram of the test card of FIG. 2 under reference lighting conditions, prior to exposure to urine.

Turning now to lighting adjustment methods, FIGS. 3A through 5B show an illustrative adjustment method that may be used in one or more embodiments. FIG. 3A shows test card 100 prior to exposure to a urine sample. The image of the test card in FIG. 3A is shown under a standard reference lighting condition. The fiducial markers on the test card may be constructed to have known colors under this reference condition. (These reference colors may be determined in a color calibration step, for example, by measuring the colors of each fiducial marker under the reference conditions.) In one or more embodiments, manufacturing methods for the test cards may be controlled to ensure that colors of each color fiducial do not deviate beyond a threshold from the reference color standard for each fiducial. These manufacturing methods may include for example using specific inks and printing processes for color uniformity, and performing quality control on the test cards to measure the color deviations.

Illustrative reference colors for the fiducial markers are as follows, expressed as triplets of (red, green, blue) intensity in the range 0 to 255. These colors are exemplary; one or more embodiments may use fiducials of any reference colors. Corner fiducial markers each have reference colors (120, 120, 120). The two rows of color fiducial markers have the following reference colors:

| Top Row | | | | | | | | | | | |
|---|---|---|---|---|---|---|---|---|---|---|---|
| R: 210 | 80 | 80 | 160 | 160 | 240 | 240 | 80 | 80 | 160 | 120 | 175 |
| G: 210 | 160 | 240 | 160 | 80 | 80 | 160 | 80 | 80 | 240 | 120 | 175 |
| B: 210 | 80 | 80 | 240 | 80 | 80 | 160 | 160 | 240 | 160 | 120 | 175 |

| Bottom Row | | | | | | | | | | | |
|---|---|---|---|---|---|---|---|---|---|---|---|
| R: 175 | 120 | 160 | 80 | 80 | 240 | 240 | 160 | 160 | 80 | 80 | 210 |
| G: 175 | 120 | 240 | 80 | 80 | 160 | 80 | 80 | 160 | 240 | 160 | 210 |
| B: 157 | 120 | 160 | 240 | 160 | 160 | 80 | 80 | 240 | 80 | 80 | 210 |

In this illustrative embodiment, the colors of the bottom row of color fiducial markers are the same as those of the top row, but in the opposite order. Thus there are 12 distinct colors for the 24 color fiducial markers, with 2 fiducial markers for each of these 12 colors. Repeating colors at offset locations may assist in developing a color correction function that incorporates location on the card, as described below.

One or more embodiments may use fewer color fiducial markers than the 24 color fiducial markers shown in FIG. 3A. For example, one or more embodiments may use 3 color fiducial markers of different colors, such as for example markers of pure red (RGB of (255, 0, 0)), pure green (RGB of (0, 255, 0)), and pure blue (RGB of (0, 0, 255)). One or more embodiments may use 9 color fiducial markers of different colors, such as for example 3 markers with 3 different shades of red (such as RGB values of (160, 80, 80), (240, 80, 80), and (240, 160, 160)), 3 markers with 3 different shades of green (such as RGB values of (80, 160, 80), (80, 240, 80), and (160, 240, 160)), and 3 markers with 3 different shades of blue (such as RGB values of (80, 80, 160), (80, 80, 240), and (160, 160, 240)). These configurations and numbers of color fiducial markers are illustrative. Any number of color fiducial markers with any set of colors, including possible repeats of certain colors, may be used in one or more embodiments of the invention.

FIG. 3B shows an illustrative image 100a of card 100 after exposure to urine (for a period of time), captured under lighting conditions that deviate significantly from the reference lighting conditions illustrated in FIG. 3A. Lighting in image 100a is also not uniform across the test card. Regions of the image 100a that correspond to fiducials on test card 100 are as follows: 320a through 320d are images of corner fiducial markers 220a through 220d, respectively; and 321a through 321d are images of illustrative color fiducial markers 221 through 221d, respectively. (For ease of illustration only 4 of the 24 color fiducial markers are labeled.) Colorimetric test regions 205a and 205f have corresponding images 305a and 305f in image 100a. (For ease of illustration only 2 of the 15 colorimetric test regions are labeled.)

Figure 4:
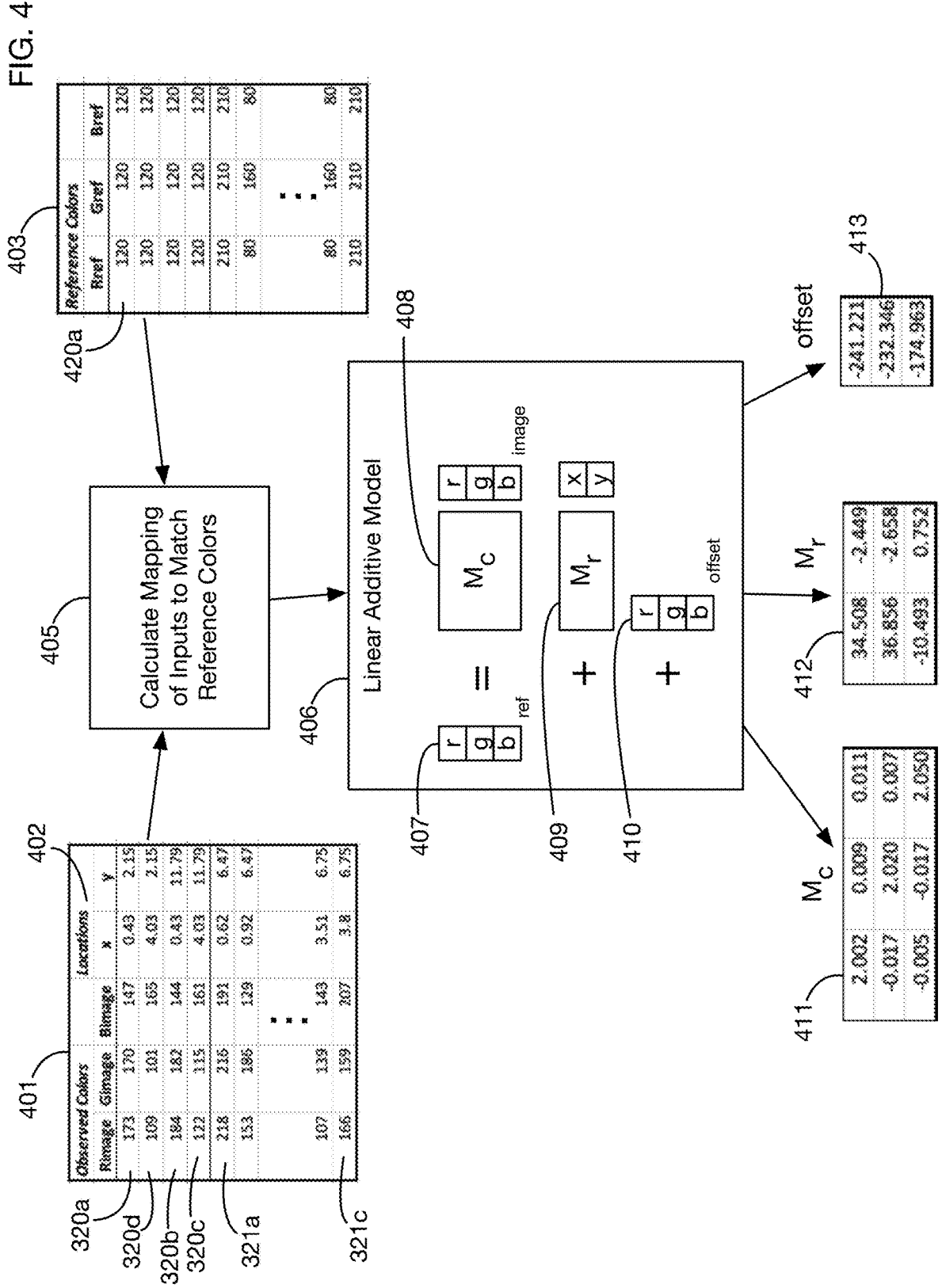
FIG. 4 shows an illustrative model for color correction that may be used in one or more embodiments.
Figure 5:
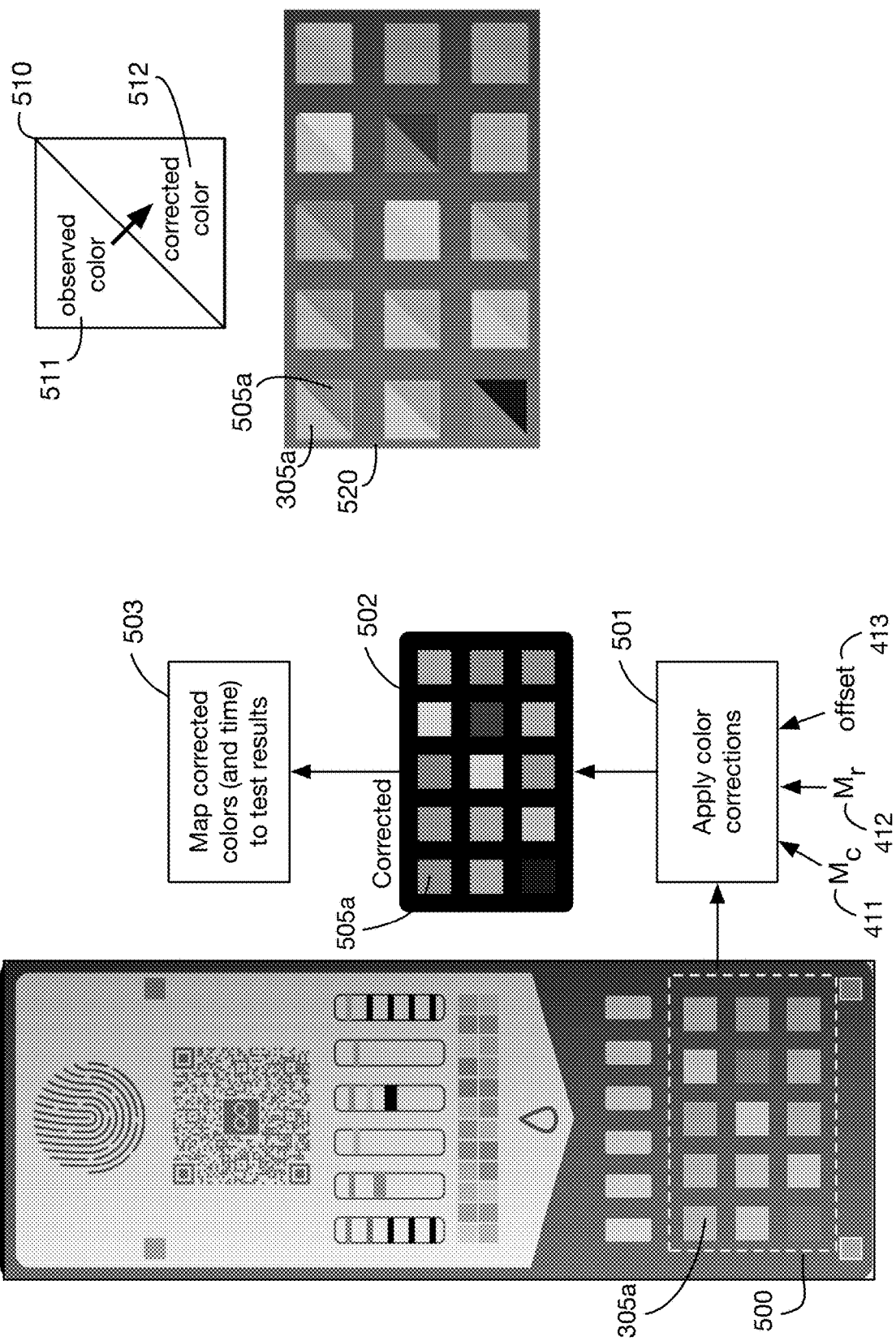
FIG. 5A shows application of the correction model of FIG. 4 to the image of FIG. 3B.
FIG. 5B compares color corrected and uncorrected images of the colorimetric tests of the test card.

FIG. 4 shows an illustrative method that may be used to derive color corrections to image 100a. The intent of the color correction process is to transform the appearance of the regions of interest in image 100a into their projected appearance under reference lighting conditions. One or more embodiments may use any desired method to determine an appropriate transformation. For example, any type of function approximation or estimation method may be used to generate a function that maps appearances into color-corrected appearances. FIG. 4 illustrates an embodiment that estimates a linear function that maps observed colors into corrected colors. This function also takes into account the position of each region of interest on the test card. A benefit of using the position as an input to the color correction function is that the correction may then compensate for non-uniform lighting conditions across the card. The use of a linear function is illustrative; one or more embodiments may use any type of linear or nonlinear function to perform color corrections.

Calculation 405 to determine the correction function receives as inputs a table 401 of the observed colors and known locations of each fiducial marker in the card, and the corresponding reference colors 403 for each fiducial marker. The locations 402 of each fiducial marker may for example be the offsets of the center of each marker from a fixed reference point on the card. Location coordinates may be measured in any units, such as for example, without limitation, pixels, millimeters, centimeters, meters, or inches. For locations that are measured in pixels, the (x,y) location values 402 may be for example integer values in one or more embodiments; for other units the location values 402 may be for example decimal values of any desired precision. Illustrative observed RGB values and locations are shown in table 401 for the corner fiducial images 320a through 320b, and for illustrative color fiducial images 321a and 321c. (The complete table may contain entries for each corner fiducial and each color fiducial, and possibly for other points on the card with known reference colors.) Table 403 contains reference colors such as those presented above. This example uses a linear additive model 406 for the mapping function from inputs 401 to outputs 403. This linear model has a parameter matrix 408 that transforms the RGB vector of observed colors into reference colors, a parameter matrix 409 that maps location vectors (x,y) into color variations, and an overall offset RGB vector 410. The location effect matrix 409 may vary based on the units in which locations vectors (x,y) are measured; for example, if the units of the location vectors are changed from pixels to millimeters, the matrix 409 may change by a scaling factor. The model 406 is additive in that the effects of the matrix multiplication 408, the matrix multiplication 409, and the offset 410 are added to obtain the final corrected color 407. Techniques such as linear regression may be used to estimate the matrices 408 and 409 and the offset 410. For the data 401 and 403, the resulting parameters for the best fit linear additive model are 411, 412, and 413.

One or more embodiments of the invention may use other functional models besides or in addition to the linear additive model 406 of FIG. 4. For example, in one or more embodiments the effect of position on color may be multiplicative instead of additive. One or more embodiments may separate the test card into zones and fit color correction functions separately for each zone. One may use machine learning techniques to obtain a mapping based for instance on a neural network or other function approximation system. One or more embodiments may use any color space in addition to or instead of RGB, such as for example HSV, HSL, or CIELAB. One or more embodiments may use other information to derive a color correction function, such as ambient light conditions sensed by a user's phone or by another image capture device. Any method that derives a mapping from observed colors to reference colors, which may optionally use other inputs such as location or ambient light sensor data, is within the spirit of the invention.

FIGS. 5A and 5B show application of the model derived in FIG. 4 to correct the colors of the image 100a of test card 100. The observed colors of regions of interest from image 100a are input into color correction process 501 along with the parameters 411, 412, and 413 derived from the appearance of the fiducial markers. For example, the 15 colorimetric test regions 500 are corrected by mapping 501 to corrected colors 502; illustrative image 305a of the upper left colorimetric test is corrected to image 505a. The corrected colors 502 are then input into process 503 that calculates test results based on the corrected colors (and on the calculated elapsed time), as described below. FIG. 5B shows the uncorrected and corrected colors of the colorimetric tests side-by-side for comparison, with legend 510 showing that the observed color 511 is shown in the upper left of the square and the corrected color 512 is shown in the lower right of the square. Table 520 shows this comparison for each of the colorimetric test regions.

Figure 6:
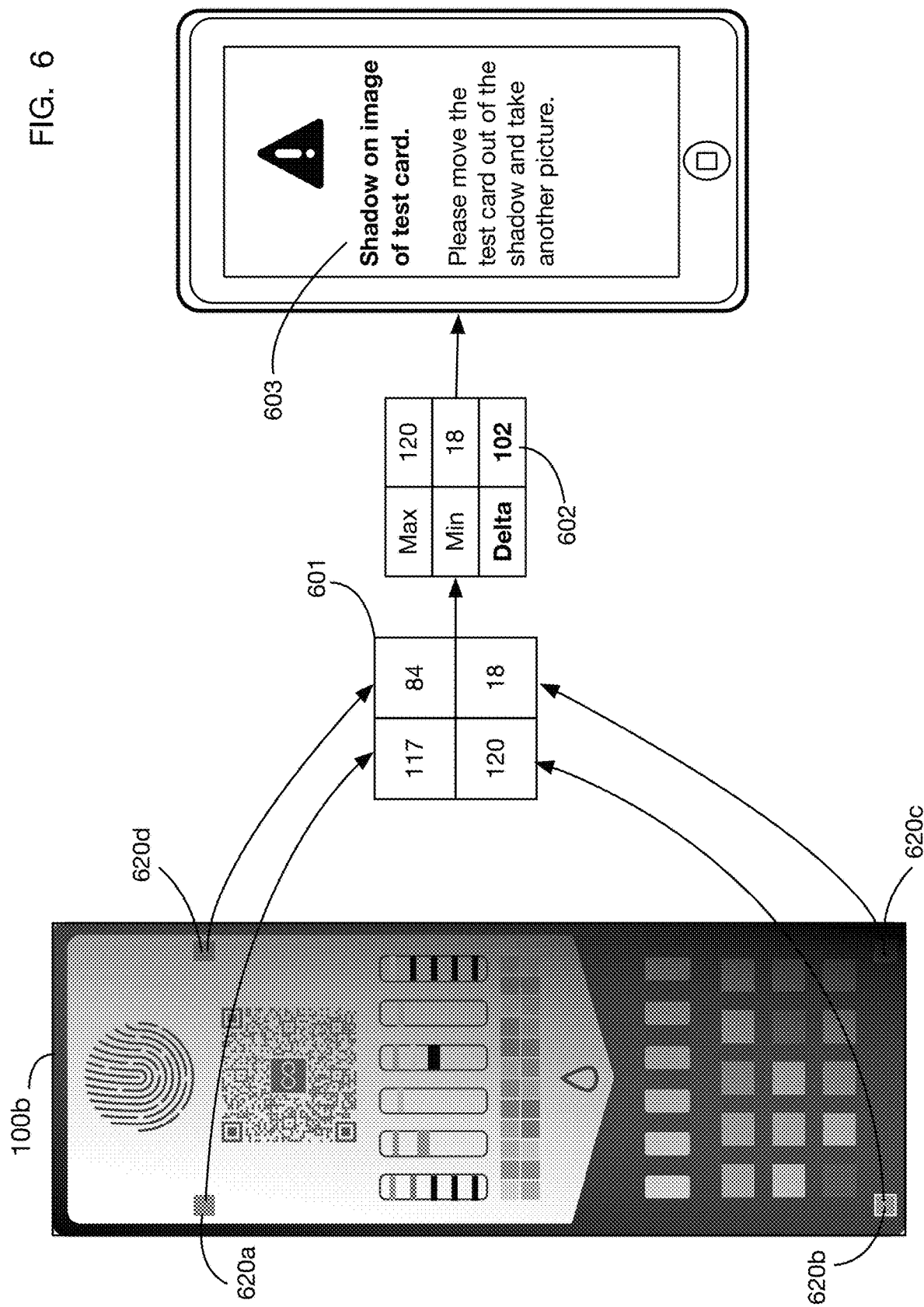
FIG. 6 shows an illustrative method that may be used in one or more embodiments to detect shadows on the test card and to inform the user that another image is needed.

In addition to color correction, one or more embodiments may analyze lighting conditions and patterns on the test card to determine whether light is sufficiently uniform or otherwise of sufficient quality for valid test results to be calculated. If issues are discovered with the lighting conditions, and these issues cannot be corrected during analysis, the system may generate an indication for the user that the captured image may not be usable. The system may prompt the user to capture another image (or to repeat the test altogether with another test card). FIG. 6 shows an illustrative example that detects a shadow on test card image 100b. One method that may be used to detect shadows is to compare the observed colors of the four corner fiducial markers; a large variance across the four fiducials may indicate a shadow. In the embodiment shown in FIG. 6, a single color value is calculated and compared for each of the four corner fiducial markers. This method is illustrative; one or more embodiments may use any combination of color channels or any single color channel (in any color space) to detect lighting anomalies. In this example, the single color value is a grayscale value. This grayscale value may be calculated using any desired transformation of RGB to grayscale; for example it may be a simple average of the R, G, and B color channels or a more complex weighted average. One or more embodiments may use any other color channel or combination thereof, such as for example lightness in an HSL color space. Grayscale values for corner fiducial images 620a through 620d are shown in table 601. A simple measure of variance for the four grayscale values may be for example the difference 602 between the maximum and minimum value. If this difference exceeds a threshold value, the system may determine that one part of the test card is heavily shadowed compared to another, and a message 603 may be displayed to the user asking the user to capture another image. In this situation, the time indicator(s) on the test card may be extremely important since the user may be capturing another image after additional elapsed time of exposure to the urine sample. Without a time indicator, capturing and using another image if the first image is unusable may not be feasible, and the entire test card may be wasted.

Figure 7:
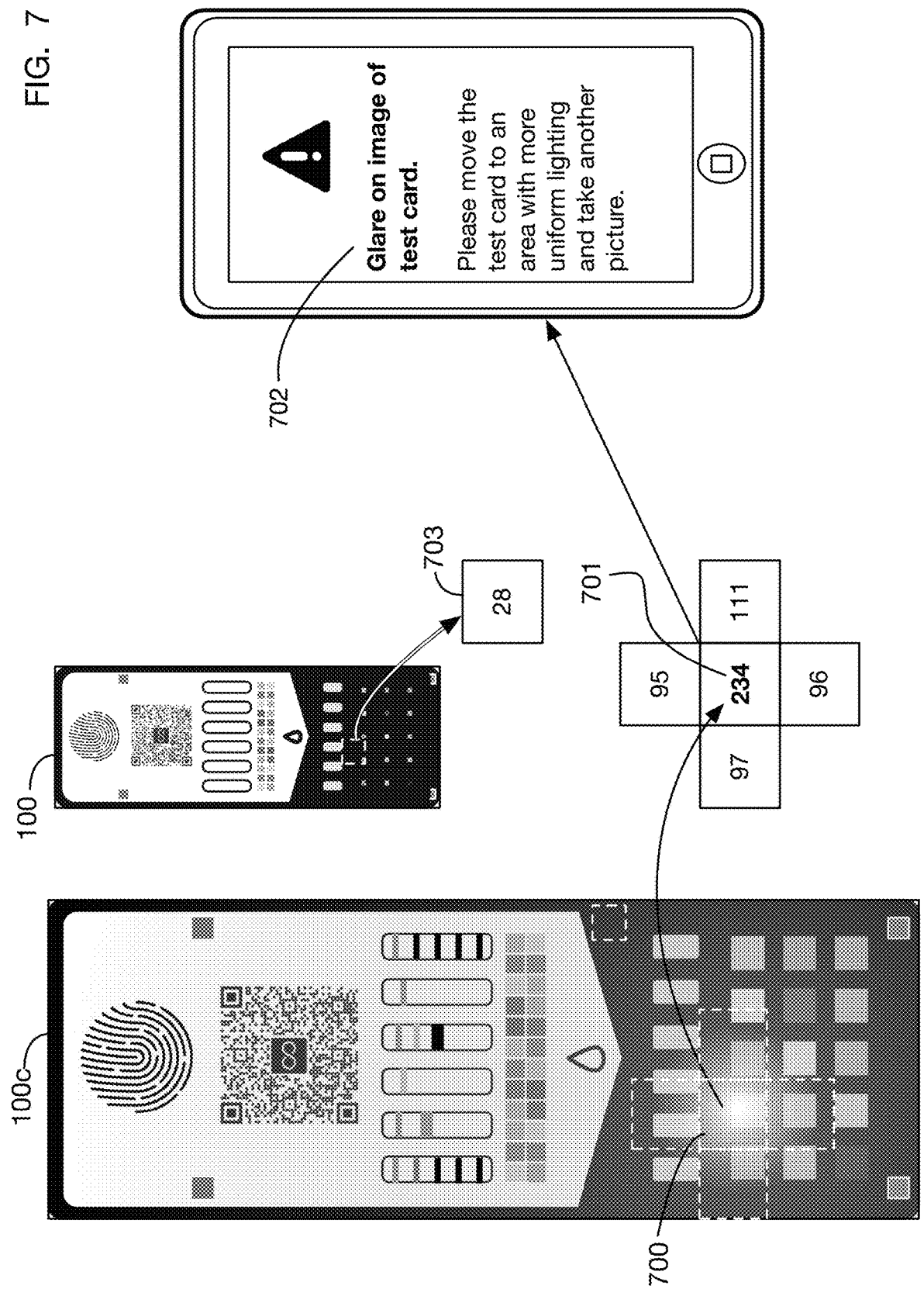
FIG. 7 shows an illustrative method that may be used in one or more embodiments to detect glare on the test card and to inform the user that another image is needed.

FIG. 7 shows an illustrative embodiment of a method to detect another lighting anomaly in a test card image. This example shows glare detection. Glare may be defined for example as a region of a test card image 100c that is much brighter or lighter than nearby regions that have similar colors or brightness under reference lighting conditions. As with shadow detection, one or more embodiments may use any color channel or combination of color channels to detect glare. The example shown in FIG. 7 uses grayscale values. For example, region 700 of test card image 100c has grayscale value 701 which is substantially greater (brighter) than the grayscale value of the surrounding regions (for example the regions above, below, left, and right). If this difference between the grayscale value of a region and that of surrounding regions exceeds a threshold value, a message 702 may be transmitted to the user indicating that glare is detected and that the user should capture another image since the existing image is not usable. In one or more embodiments, glare may be defined instead as an excessive difference between the observed value 701 of a region and the expected value 703 of that region under reference lighting conditions.

Figure 8:
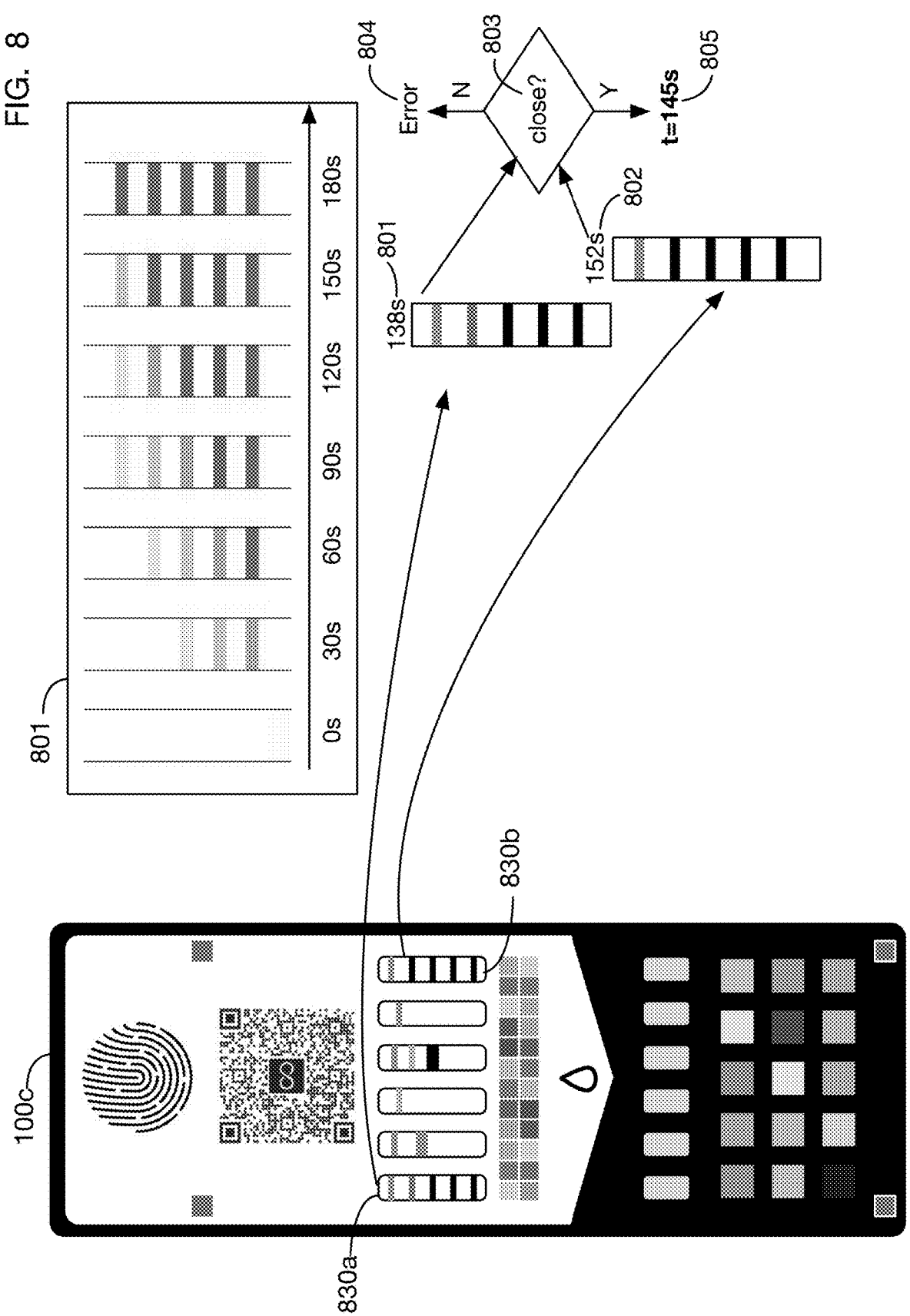
FIG. 8 shows an illustrative method that may be used in one or more embodiments to calculate the elapsed time of exposure to a urine sample from the appearance of one or more time indicators on the test card.

FIG. 8 illustrates how the time indicator or indicators of a test card may be used in one or more embodiments to calculate the elapsed time of exposure to a urine sample. In this illustrative embodiment, the test card has two time indicators; in image 100c of the test card (after exposure) these two time indicators have appearances 830a and 830b. In one or more embodiments these time indicator appearances may be color corrected as described above for colorimetric test regions; color correction is not shown in FIG. 8 for ease of illustration. In this embodiment, time indicators are lateral flow assays with multiple target lines that become visible as the urine sample flows along the assay membrane. The number of visible lines and the intensity of the lines varies with the time of exposure. The time indicator may for example use antibodies that are non-human (such as donkey-anti-goat and goat-anti-mouse), and may use no human antibodies, which means they should not be sensitive to human variables; thus the intensity of the target lines in the time indicator will be affected only by exposure time and not by the presence or absence of specific analytes in the urine sample. (These antibodies may also be used for control lines in other lateral flow assays on the test card.)

The time indicators may be configured to minimize the effect of environment factors such as temperature and humidity on the visibility and intensity of test lines, so that the timing factor can be isolated and measured. Within the expected range of ambient temperatures during use, temperature should not have a significant impact on the time indicator results. In case of extreme high or low temperatures, the timer will be affected the same as the lateral flow strips thereby doubling as a control for ambient temperature. If the user's phone can sense ambient temperature, that information can also be used in one or more embodiments to adjust results for extreme temperatures or other environmental factors.

The relationship between visibility and intensity of test lines and exposure time may be determined for example using calibration experiments. Table 801 shows an illustrative calibration run showing the appearance of test lines of a reference time indicator at different elapsed times to a reference urine sample. Using this calibration data 801, one or more embodiments may obtain an elapsed time estimate by finding a closest match between the observed intensity of test lines and a point on the calibration curve 801. Interpolation may be performed between points on the curve 801 if the observed test line intensities lie between two values. For example, test indicator 830a may correspond to an interpolated elapsed time 801, and test indicator 830b may correspond to an interpolated elapsed time 802. In one or more embodiments, elapsed times from multiple time indicators may be compared in test 803, and if they are too far apart it may indicate an error 804 (for example because the urine sample was not distributed uniformly across the test card). If values are reasonably close, a combined estimate 805 may be generated, for example as an average of the elapsed time estimates from the different time indicators.

Figure 9:
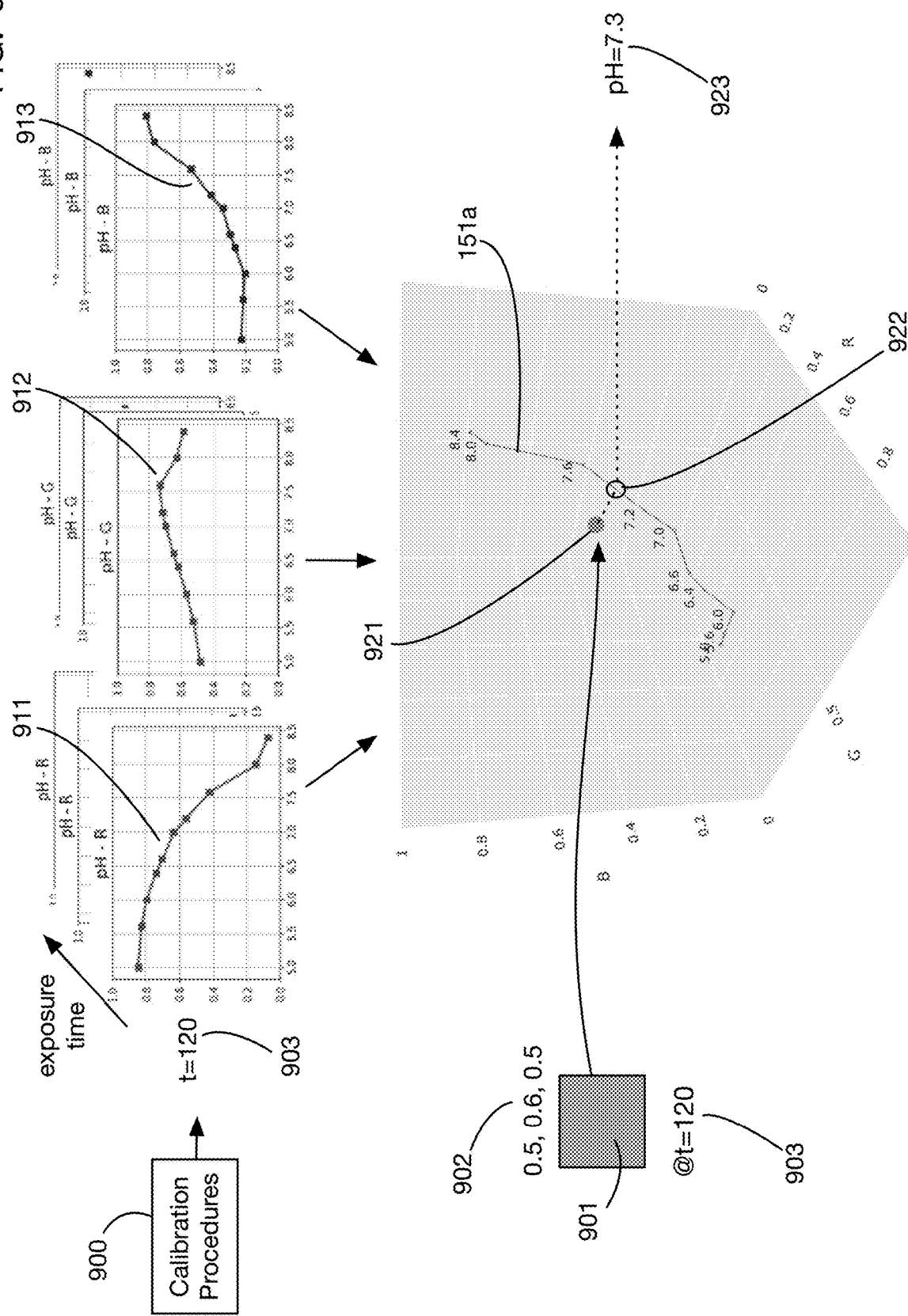
FIG. 9 shows an illustrative calculation of a test result from color corrected images and from calibration curves.

FIG. 9 shows an embodiment of a calculation of a test result from color-corrected appearance and from the time estimate obtained from time indicators. For illustration this calculation is shown for a colorimetric test; a similar procedure may be used for a lateral flow assay or other test region. The color-corrected appearance 901 of a colorimetric test region may be expressed as a triplet of RGB values 902 (shown here in the range of [0,1] for each color channel). An elapsed time estimate 903 is available from analysis of the time indicator or indicators on the test card. The color 902 and time 903 are compared to a sequence of calibration curves that are generated for example using calibration procedures 900. These calibration procedures 900 may for example measure the color of a colorimetric test region with different quantities of the test analyte in the sample, and at different exposure elapsed times. For example, the illustrative calibration curves 911, 912, and 913 show the R, G, and B colors, respectively, as a function of sample pH, after an exposure elapsed time of 903. Similar curves are obtained for other exposure times. For a specific elapsed time 903, the three curves 911, 912, and 913 may be combined into a 3D curve 151a in RGB space; each point on this curve corresponds to a pH value. The observed color 902 maps to a point 921 in this 3D RGB space. One or more embodiments may for example locate the point on curve 151a that is closest to the observed color point 921, and use that point as the test result. If this point lies between calibration points, a result value 923 may for example be calculated by interpolating between points on the curve corresponding to known pH values. One or more embodiments may use any method to interpolate between calibration points, including but not limited to linear interpolation.

Figure 10:
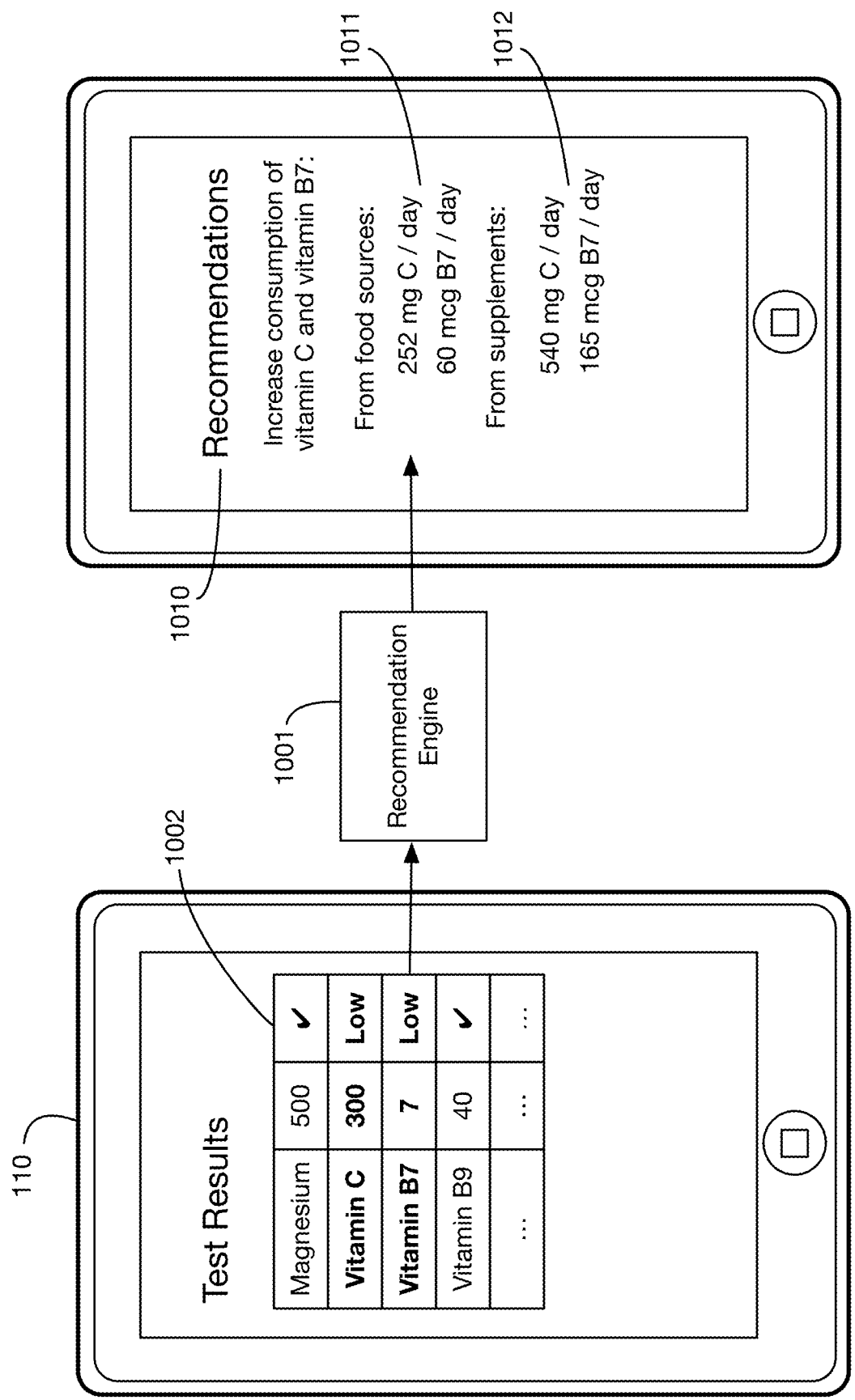
FIG. 10 shows an illustrative embodiment with a recommendation engine that generates nutritional recommendations based on urine test results.

In one or more embodiments, the test system may include a computer specifically configured to analyze test results and generate nutritional or lifestyle recommendations. Embodiments of the computer are referred to herein as a recommendation engine. FIG. 10 shows an illustrative example. Analysis of a urine test card may generate test results 1002, which may include measurements of substances that are affected by nutrition, such as vitamins and minerals. If one or more of these substances are outside expected or normal ranges, a recommendation engine 1001 may analyze the test results 1002 to develop nutritional recommendations 1010. The recommendation engine 1001 may execute on any processor or processors. For example, it may execute on mobile device 110 used by a user, or on cloud-based servers, or on any combination of processors. In the example shown in FIG. 10, test results for two substances—Vitamin C and Vitamin B7—are below normal ranges. The recommendation engine 1001 therefore generates recommendations to increase consumption of these substances, either from food sources or from supplements (or from combinations thereof). The recommendation engine may recommend specific amounts 1011 to consume from food and amounts 1012 to consume from supplements. The recommended consumption amount from supplements may in some cases exceed those from food because absorption of certain substances from food may be more efficient than from supplements. In some situations, the recommended consumption of some substances from supplements may be lower than the recommended consumption of those substances from food, for example if certain substances may be detrimental when consumed in large doses in supplements or if they are safer to obtain from food. The recommendation engine 1001 may take into account these different levels of absorption in developing recommended quantities 1011 and 1012.

One or more embodiments may make suggestions or recommendations for behavioral or lifestyle modifications, in addition to or instead of nutritional recommendations. For example, one or more embodiments may measure substances that correlate with stress, such as cortisol; if these substances are trending up or down from a known health range (which may differ across users), stress reduction techniques such as meditation, exercise, or sleep may be recommended. In one or more embodiments, the system may recommend adding a certain number of minutes of activity per day, where the number of minutes added may be based on how much a cortisol level (or a level of one or more other substances) deviates from the normal or health range. The system may recommend an amount of activity and may let the user choose from a list of activities, such as for example walking, exercise, yoga, meditation, or sleep. One or more embodiments may measure substances that are correlated with how well a person is hydrated, and may recommend adjustments to water or fluid consumption accordingly. For example, hydration status may be calculated based on the specific gravity of the urine. If a user is under-hydrated, the system may recommend drinking more fluids; if the user is over-hydrated, the system may recommend reducing fluid consumption or consuming electrolytes.

Figure 11:
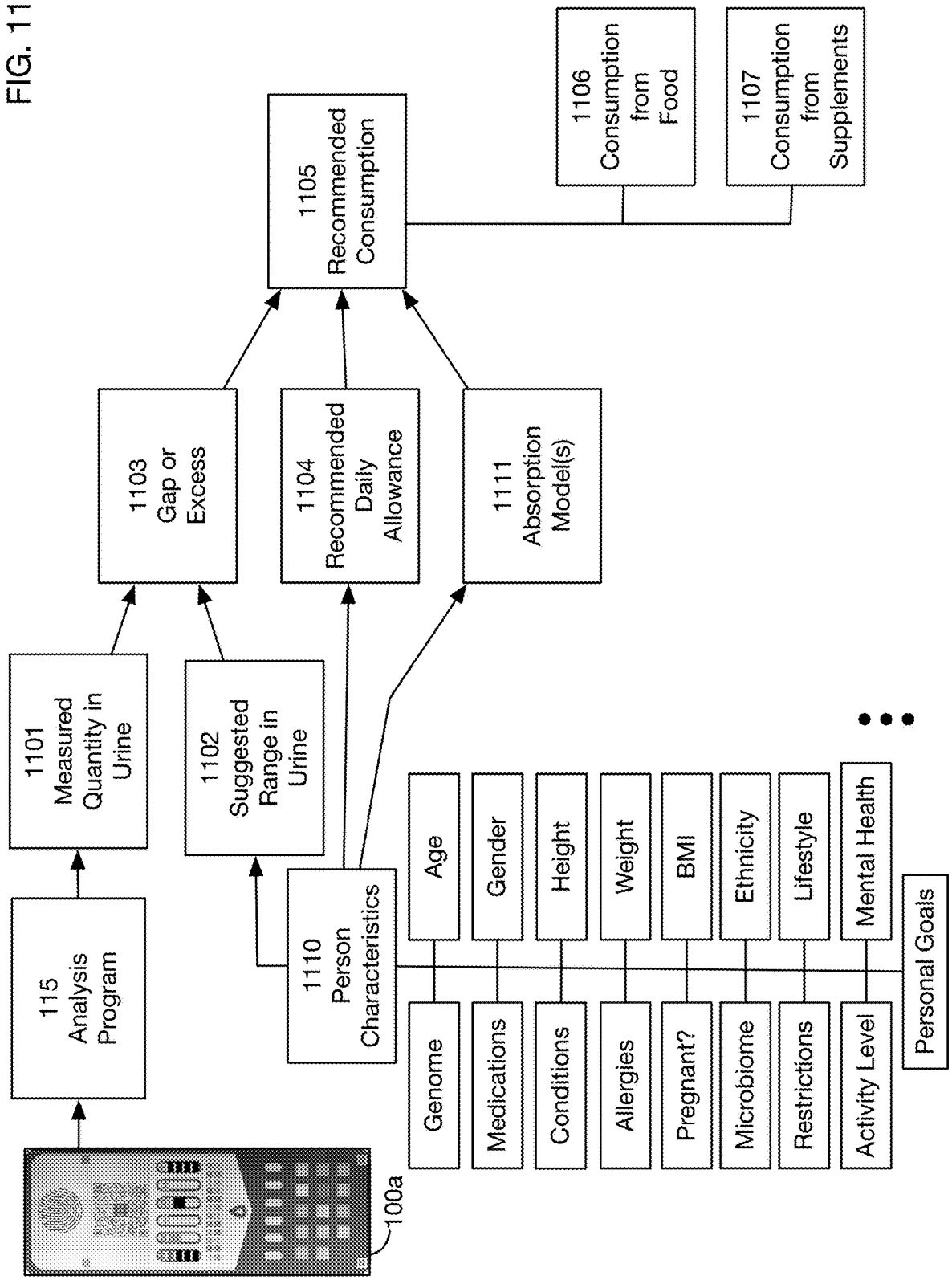
FIG. 11 shows a data flow diagram for an illustrative recommendation engine.

FIG. 11 shows an illustrative data flow diagram for an embodiment of a recommendation engine. This diagram shows how the recommendation engine may use various factors and data sources to develop consumption recommendations such as recommendations 1011 and 1012 in FIG. 10. One or more embodiments may develop consumption recommendations using only a subset of the factors shown in FIG. 11. As described above, an image 100a of a test card that has been exposed to a urine sample is analyzed by analysis program 115, resulting in test results 1101. These results 1101 may for example include the measured quantity in the urine sample of one or more substances. The quantity 1101 of a substance may be measured on any quantitative or qualitative scale; the scale may be continuous or discrete. For one or more of these substances, the measured quantity 1101 may be compared to a suggested or expected range 1102. This range 1102 may represent a range of normal or typical values for the test result. It may depend on one or more characteristics 1110 of the person whose urine is tested. These characteristics may include for example, without limitation, the person's age, gender, height, weight, body mass index (BMI), and ethnicity. They may also or instead include any data on the person's genome or microbiome, medications the person is taking, medical conditions the person has, the person's mental health, allergies the person has, dietary restrictions, characteristics of the person's lifestyle or activity level, the person's personal goals, and situations such as whether the person is pregnant or lactating. These characteristics are illustrative; one or more embodiments may take into account any data related to any aspect of the person who is tested.

Comparison of the measured quantity 1101 of a substance to the suggested range 1102 may identify a gap or excess 1103 between the observed and the desired or expected range. If there is a gap, then the recommendation engine may recommend additional consumption of the substance. If there is an excess, then the recommendation engine may in some situations recommend a reduction in the consumption of the substance. (In some situations it may be unnecessary or inadvisable to recommend a reduction, for example if the amounts of the substance above the desired range are not harmful; in these cases the recommendation engine may recommend making no changes to the current level of consumption.) The amount of additional or (in some situations) reduced consumption 1105 may depend on several factors in addition to the amount of gap or excess 1103. For example, for some substances there may be a recommended daily allowance (RDA) 1104 of the substance, which serves as a baseline consumption that should yield normal results. This RDA may in turn depend on some of the characteristics 1110 of the person; for example, an adult male may have a different RDA for a substance than a female child. Another factor that may affect the recommended consumption 1105 is the degree to which the desired substance is absorbed from food or supplements. The recommendation engine may use or generate models 1111 of the extent of absorption, which may affect the calculations of the recommended consumption 1105. Because absorption models 1111 may differ between food and supplements, the recommended consumption 1105 may include a recommended consumption 1106 from food, and a recommended consumption 1107 from supplements, which may be different from the consumption 1106 from food.

FIG. 12 shows an illustrative table of RDA 1104 as a function of selected characteristics 1110 of the person. Values differ between male RDAs 1104 and female RDAs 1104b. They also vary by age. For example, the RDA 1201 is the recommended consumption for an adult male.

Figure 13:
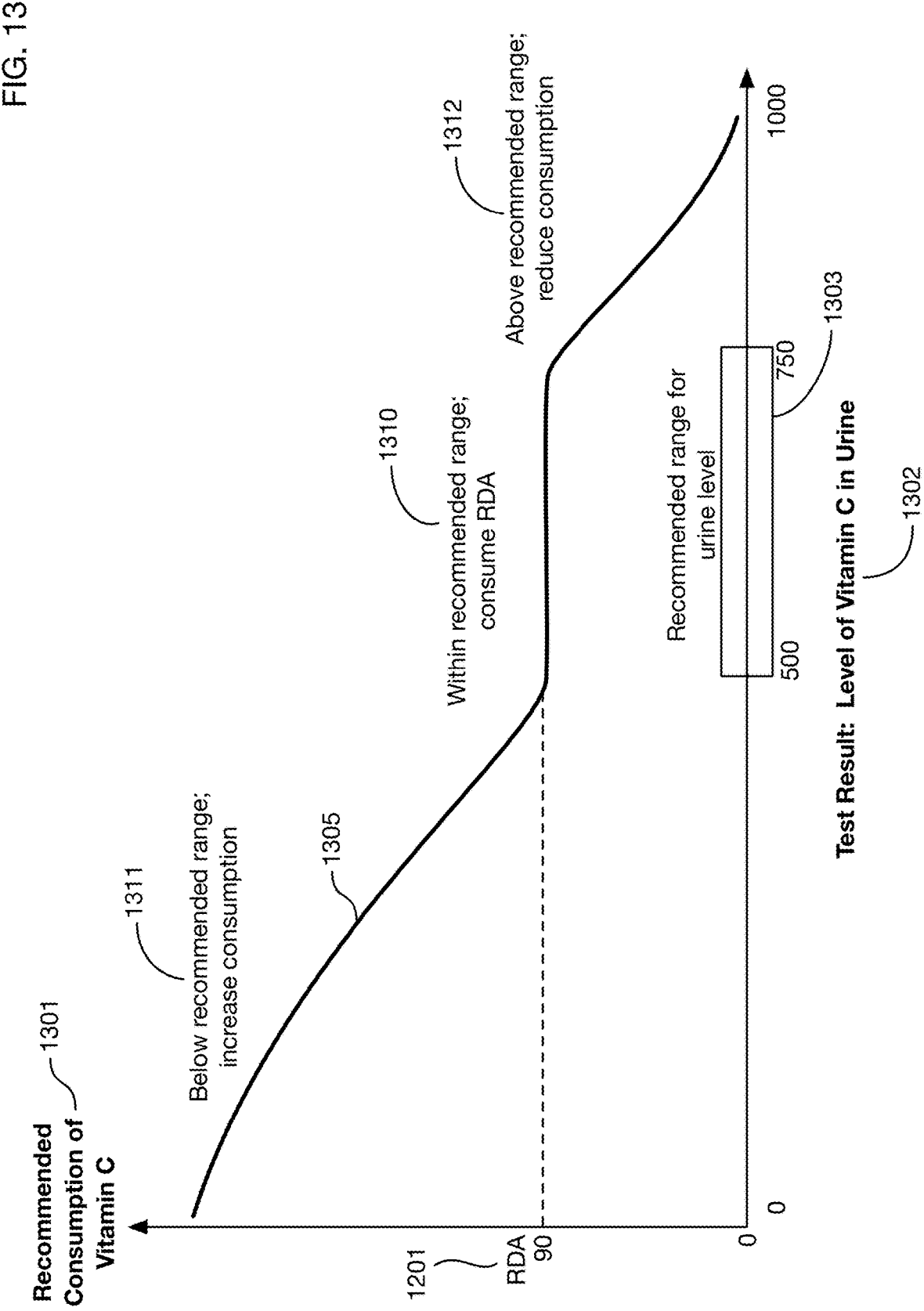
FIG. 13 shows a conceptual graph that relates urine test results for Vitamin C to recommended consumption.

FIG. 13 shows a conceptual framework for calculation of recommended consumption 1105 based on test results. This example illustrates a calculation for Vitamin C for an adult male; other substances and other person types may have similar frameworks but with different specific values and relationships. A recommended consumption curve 1305 relates the test result level 1302 to a recommended consumption amount 1301. A recommended range 1303 for the test result corresponds to sufficient nutritional intake; this range may depend on factors such as the characteristics of the person being tested. If the test result is within this range 1303, the recommended consumption 1310 may be at or near the recommended daily allowance 1201 for the substance (which may also depend on characteristics of the person). If the test result is below this range 1303, the recommended consumption 1311 may be above the RDA 1201. If the test result is above the range 1303, in some situations it may be appropriate to reduce consumption 1312 below the RDA 1201, particularly if excess amounts of the substance may be toxic. For some substances, having levels above the recommended range 1303 may not be dangerous or detrimental, in which case continued consumption of the RDA 1201 in range 1312 may be appropriate.

In one or more embodiments, the test result value 1302 for a substance (such as Vitamin C) may be measured or reported as a value selected from a discrete set of values, such as "Very High", "High", "Medium", "Low", or "Very Low" for example. Any classification scheme with any number of discrete values may be used. These discrete values may correspond for example to ranges or "buckets" of quantitative results. For example, a Vitamin C level from 0 to 200 may be reported as "Very Low", a level between 200 and 500 may be reported as "Low", and so on. Any ranges or buckets of any size may be used; these ranges or buckets may be of the same size or of different sizes. In one or more embodiments, quantitative discrete values may be used instead of qualitative labels, for example, test result values may be reported as integers in the range of 1 to 5, 1 to 10, or within any desired range or in any desired set. Quantities of substances may be measured on any qualitative or quantitative scale; the scale may be continuous or discrete.

In one or more embodiments, the recommended consumption 1301 may also be selected from a set of discrete values. These values may correspond to specific buckets or ranges for the measured quantity 1302 of the substance, as described above.

The recommended consumption curve 1305 may be of any shape. One or more embodiments may use a piecewise linear curve, as illustrated for example in FIG. 14 and FIG. 15. In the embodiment shown in FIG. 14, the substance level 1302 is mapped into a substance level score 1401 with a piecewise linear curve. This score 1401 represents how closely the measured substance level is to the desired range 1303; within the desired range the score is set to 100% (1402). This normalized value 1402 is arbitrary; one or more embodiments may normalize to any desired value within the recommended range 1303. A deviation score 1403 is then derived from the score 1401; the deviation may be for example the normalized value 1402 minus the score. The deviation represents how far away the measured value 1302 is from the recommended range. However, the maximum deviation (100% in FIG. 14) may be reached at a level 1404 above 0, if it is advisable at this level 1404 to consume a maximum amount of the substance. The level 1404 at which the deviation curve saturates may be set for example based on expert assessment of how quickly consumption of the substance should be increased as test results fall below the recommended range 1303.

Figure 14:
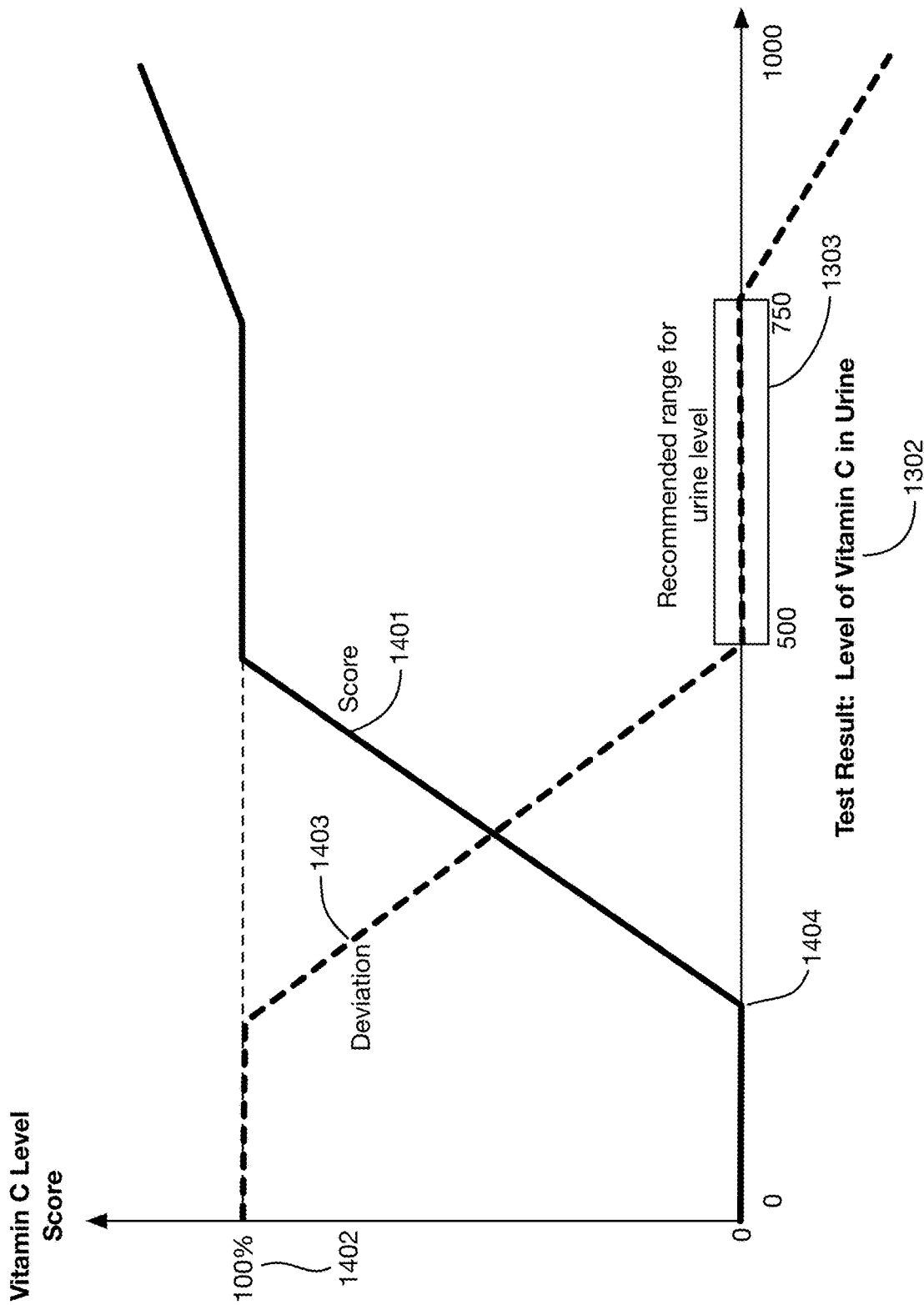
FIG. 14 shows an illustrative scoring graph that maps urine test results for Vitamin C to a percentage score, where a deviation of this score from ideal (100%) may be mapped into a recommended consumption.

The score 1401 and deviation 1403 in the illustrative example of FIG. 14 are piecewise linear with 4 regions: a first region below level 1404 where the score is 0% and the deviation is 100%, a second region between level 1404 and the recommended range 1303, where the score increases linearly from 0% to 100%, a third region within the range 1303 where the score is 100%, and a region above the recommended range 1303 where the score goes above 100%, indicating excess consumption. This structure is illustrative; one or more embodiments may use score curves with any number of regions; scores may increase, decrease, or remain level at any points of the curve, and slopes may be set to any desired values. In one or more embodiments, scores may be selected from a set of discrete values rather than calculated on a continuous scale.

Figure 15:
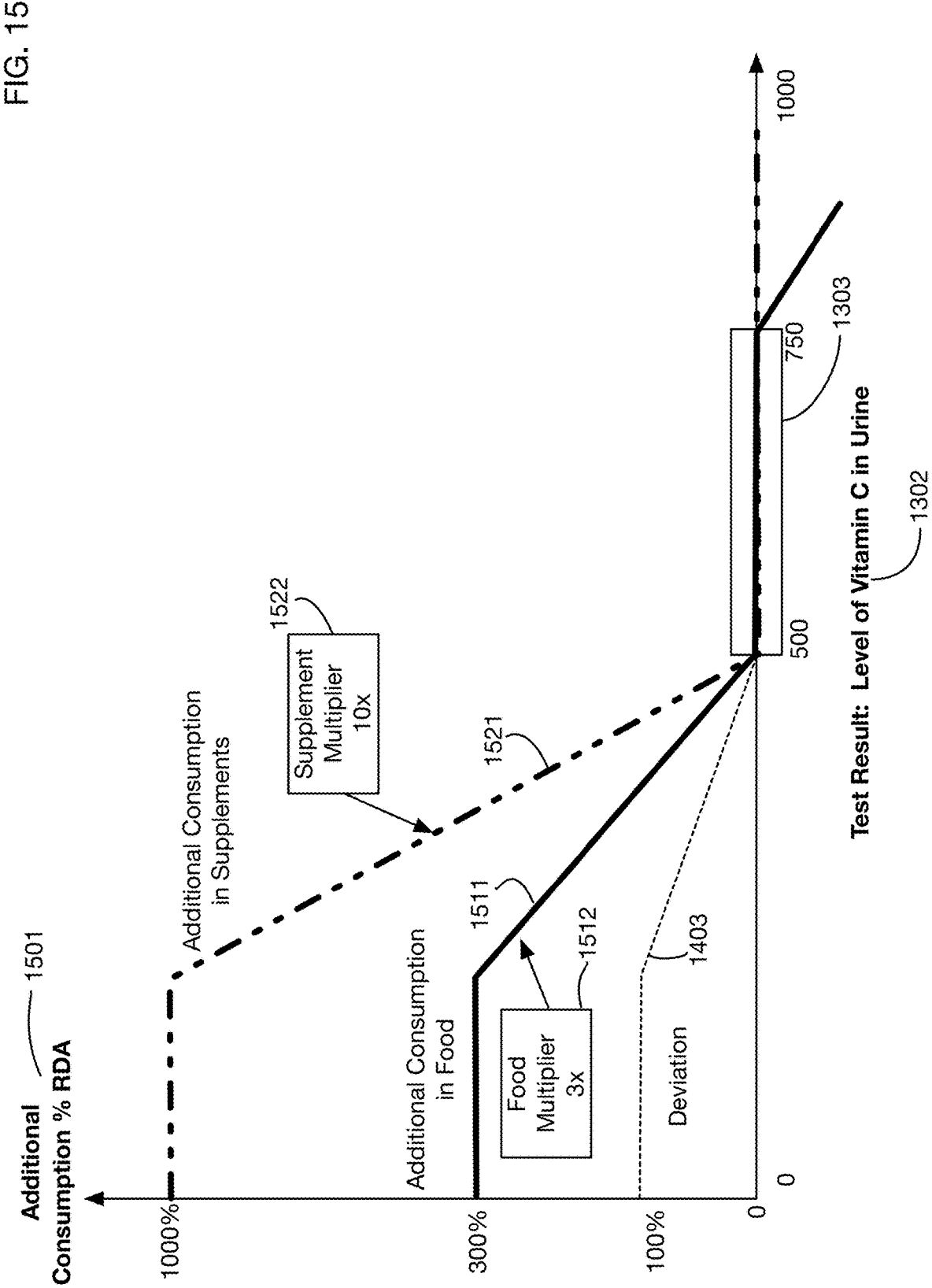
FIG. 15 continues the example of FIG. 14 to show how the deviation percentage may be mapped into recommended consumption of Vitamin C in either food or supplements.

FIG. 15 continues the example of FIG. 14 to illustrate how the deviation score 1403 may be used to calculate additional consumption of the substance. In this example, the deviation 1403 is multiplied by a multiplication factor to yield the additional recommended consumption 1501 as a percentage of the recommended daily allowance. There is therefore a linear relationship between the deviation score and the recommended additional consumption. The multiplication factor differs for food and supplements. In this example the food multiplier 1512 is 3, and the supplement multiplier 1522 is 10; this difference may reflect more efficient absorption of Vitamin C from food than from supplements. These different multipliers are examples of absorption models 1111 as discussed with respect to FIG. 11. Curve 1511 shows the recommended additional consumption of Vitamin C in food as a function of the test result value 1302, and curve 1521 shows the recommended additional consumption of Vitamin C in supplements as a function of the test result value. These curves show additional consumption above the RDA. For test results above the recommended range 1303, the additional food consumption curve 1511 becomes negative, indicating that the consumption of Vitamin C in food should be decreased below the RDA. Above and within the recommended range 1303, the additional supplement consumption curve 1521 is zero, because no supplementation is indicated.

Figure 16:
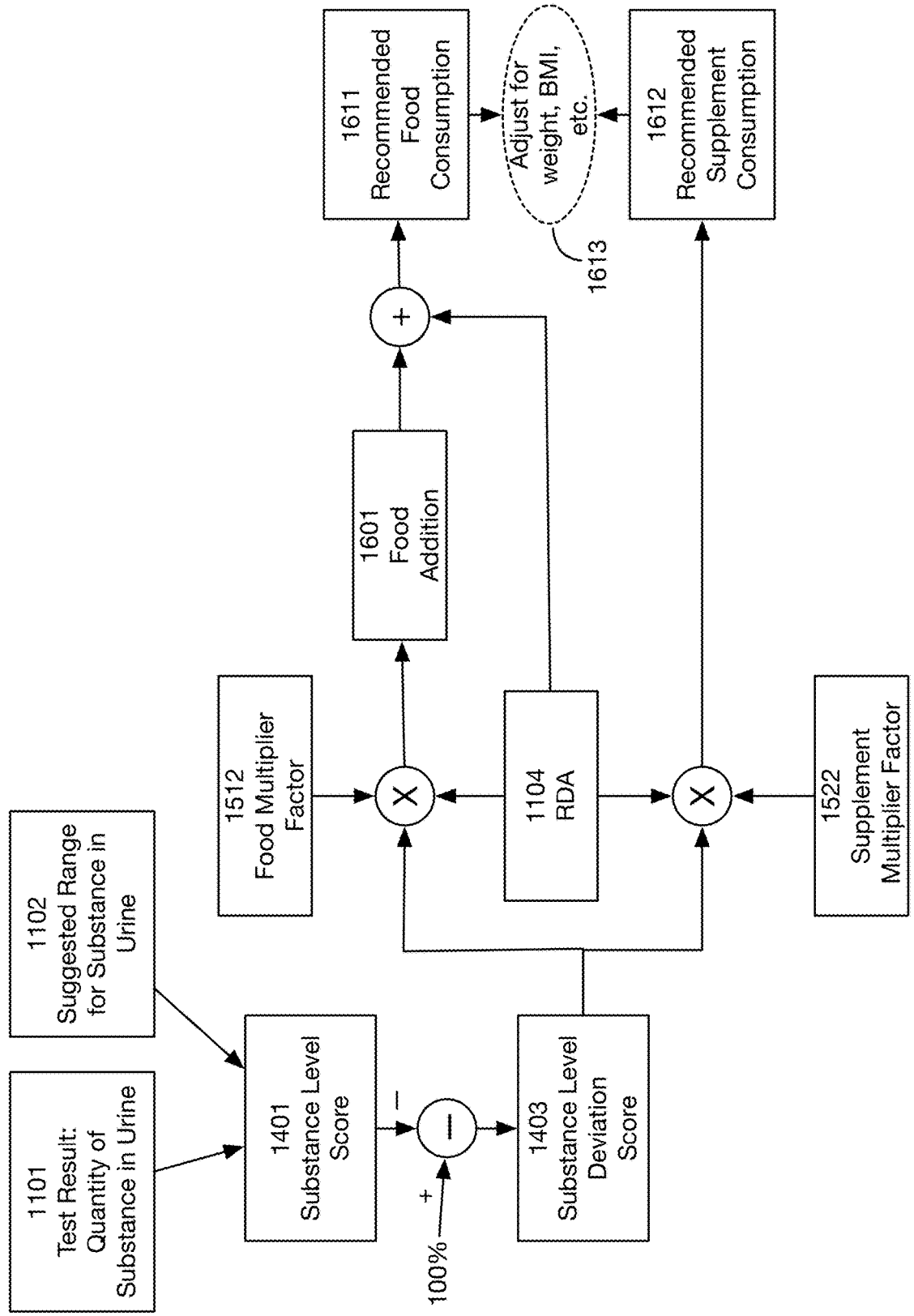
FIG. 16 shows an illustrative algorithm that calculates the recommended consumption of a substance in food or supplements based on test results, a recommended daily allowance, and multiplier factors for food and supplements.

FIG. 16 shows illustrative calculations that may be used in one or more embodiments to determine recommended consumption of a substance in either food or supplements. As described with respect to FIG. 14, a substance level score 1401 is determined based on a comparison of the quantity of the substance detected in the urine sample 1101 and the suggested range 1102. This substance level score may for example be a piecewise linear function of the quantity 1101, although one or more embodiments may use any function including nonlinear functions. The deviation score 1403 is then calculated as 100% less the substance level score 1401. As described with respect to FIG. 15, the deviation score 1403 is then multiplied by a food multiplier factor 1512 to obtain a food addition as a percentage of RDA 1104; multiplying this product by the RDA yields the food addition 1601. This value 1601 represents the additional consumption of the substance above the RDA; adding the RDA 1104 to the addition 1601 yields the total recommended consumption of the substance in food 1611. Similarly the product of the deviation 1403, the supplement multiplier factor 1522, and the RDA 1104 yields a recommended consumption 1612 in supplements. In one or more embodiments, the recommended food consumption 1611 and recommended supplement consumption 1612 may be further adjusted for factors 1613 such as weight, body mass index, or other characteristics of the person.

One or more embodiments may use variations of the algorithm illustrated in FIG. 16 to calculate recommended consumption of a substance in food or supplements. For example, in one or more embodiments the food multiplier factor 1512 and the supplement multiplier factor 1522 may vary based on the deviation score 1403 or based on other factors. In one or more embodiments, recommended consumption calculations may take into account synergistic or antagonistic effects across different substances; for example, consumption of one substance may increase or decrease absorption of another substance.

Figure 17:
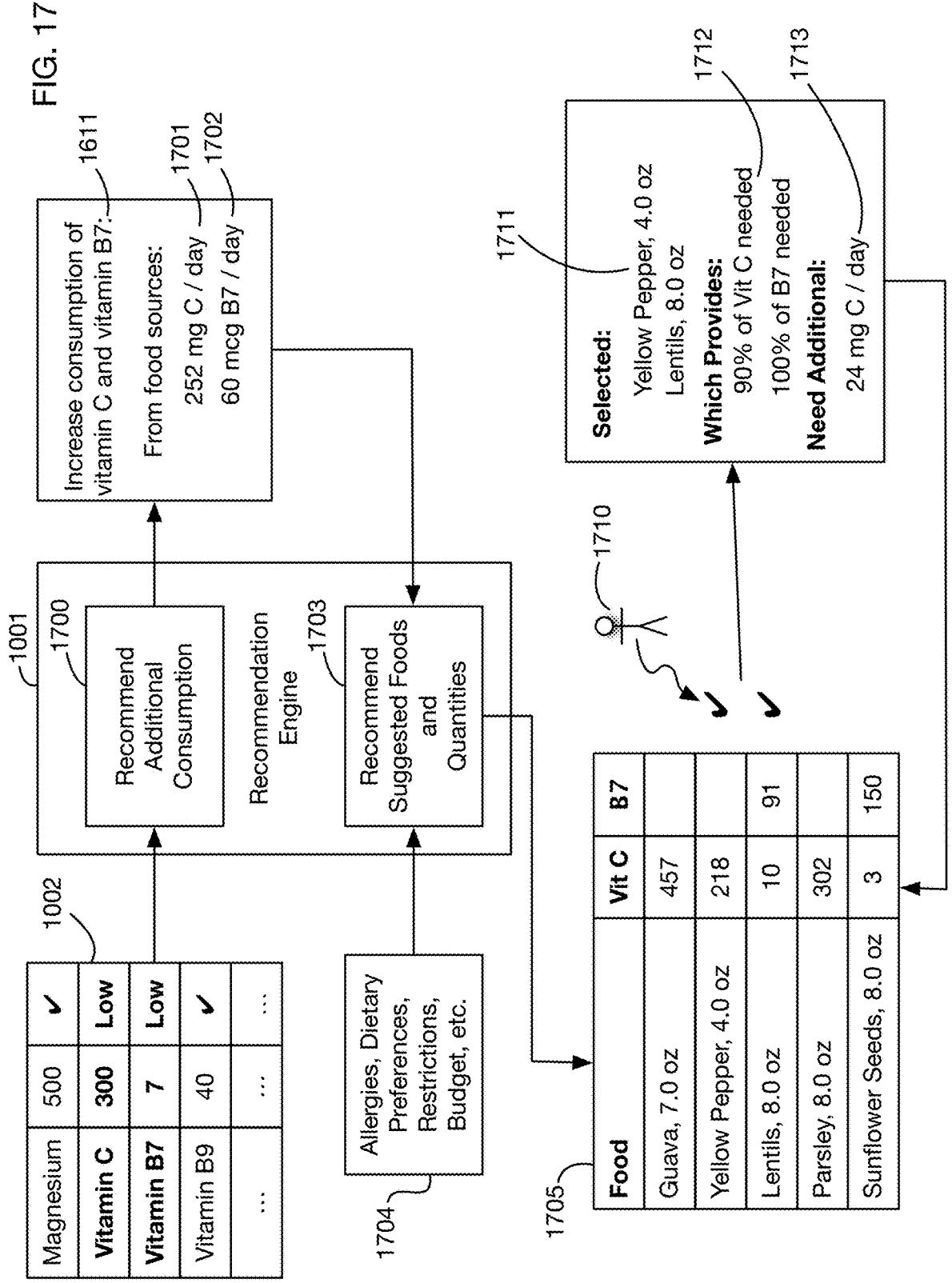
FIG. 17 illustrates a computer specifically configured to recommend specific foods, herein referred to as a recommendation engine to provide the recommended additional consumption of nutrients.

In one or more embodiments the recommendation engine may also recommend specific foods and specific quantities of these foods to meet the recommended amount of consumption of one or more substances. FIG. 17 shows an illustrative example using the test results 1002 of FIG. 10. The recommendation engine 1001 performs calculations 1700 to determine increases 1611 in consumption of two substances, and makes specific recommendations for additional consumption in food 1701 of Vitamin C and additional consumption in food 1702 of B7. In addition, it performs analysis 1703 to generate a list 1705 of recommended or candidate foods and quantities of these foods that may be used to obtain the recommended amounts 1701 and 1702. In one or more embodiments these suggested foods may be based as well on other factors 1704 such as allergies, dietary preferences or restrictions (such as whether the person is vegetarian or gluten sensitive), and budgets. The user 1710 may select specific items from the list 1705, and as the selections are made the system may display information such as the selected items 1711, the fraction 1712 of the suggested amounts of substances that are provided by the selected items, and the remaining amounts 1713 for which additional selections are needed. This process may be iterative, and the user may add or modify the selected items until they include the amounts 1701 and 1702.

Figure 18:
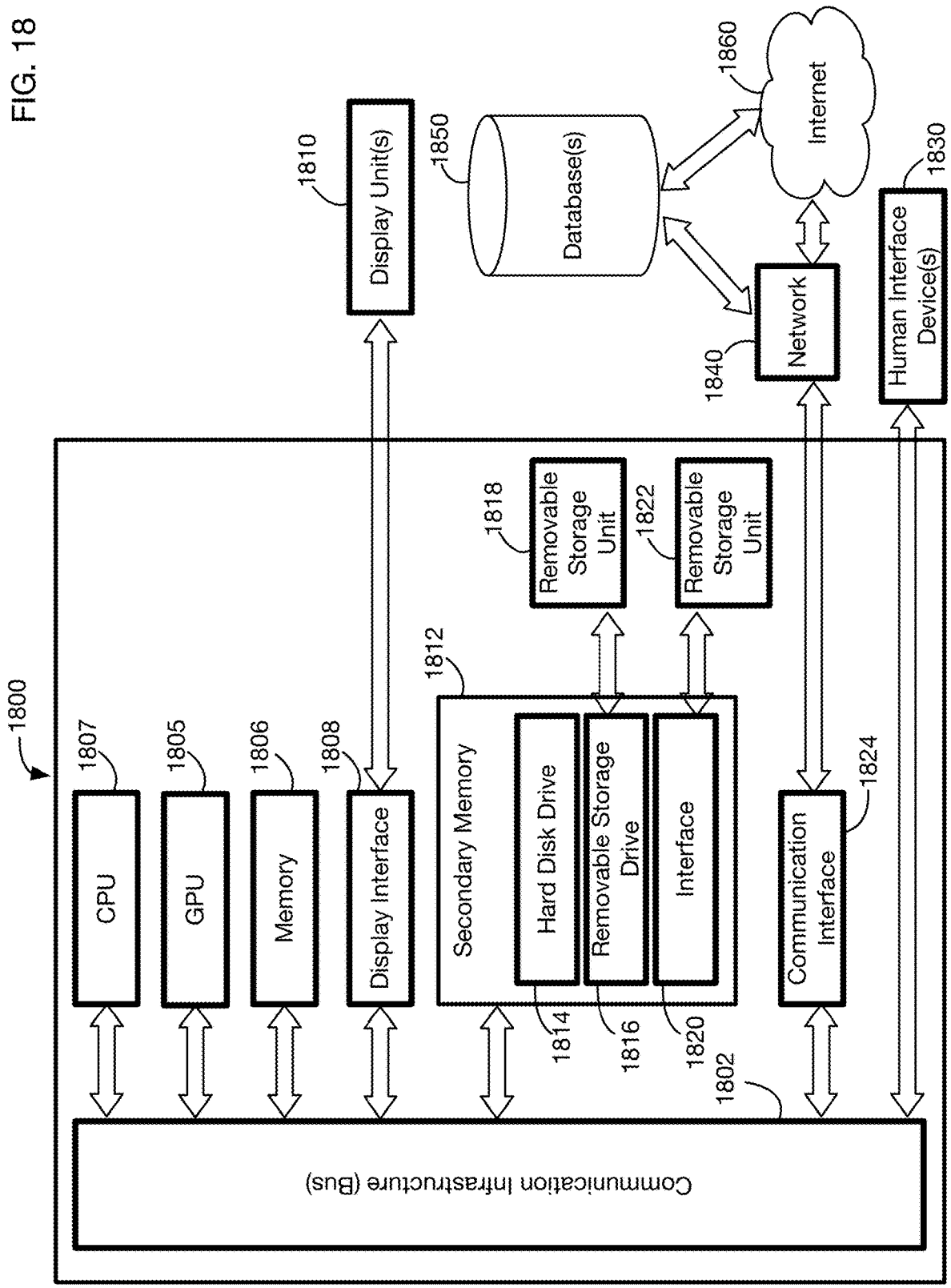
FIG. 18 shows illustrative computer hardware that may be used in one or more embodiments to perform any or all of the functions of the system, including for example analysis of test cards and generation of nutritional recommendations.

FIG. 18 shows an embodiment of exemplary computer 1800 that may be utilized in, by, or as any component in the system. In one or more embodiments, computer 1800 may be a network of computers, each of which may have any or all of the components shown in FIG. 18. In one or more embodiments, computer or computers 1800 may also be utilized to implement any function in the system, i.e., any step or act or function that executes in any computer or server or engine in the system. For example, without limitation, computer or computers 1800 may capture test card images, analyze these images to determine test results, and generate recommendations based on these test results. Computer or computers 1800 may be or may include for example mobile device 110. Computer 1800 may include processor CPU 1807 that executes software instructions specifically tailored to the respective functions of embodiments of the invention. The software instructions, otherwise known as computer program instructions, may reside within memory 1806. Computer 1800 may include processor GPU 1805, which may execute graphics instructions or other instructions for highly parallel operations, for example. GPU program instructions may also reside within memory 1806. Computer 1800 may include display interface 1808, which may drive display unit or units 1810 of any computer in the system as desired. Some computers 1800 may or may not utilize a display. Computer 1800 may include communication interface 1824, which may include wireless or wired communications hardware protocol chips. In one or more embodiments of the invention communication interface 1824 may include telephonic and/or data communications hardware. In one or more embodiments communication interface 1824 may include a Wi-Fi™ and/or BLUETOOTH™ wireless communications interface. Any wireless network protocol or type may be utilized in embodiments of the invention. CPU 1807, GPU 1805, memory 1806, display interface 1808, communication interface 1824, human interface devices 1830, secondary memory 1812, such as hard disk 1814, removable storage 1816, secondary memory interface 1820 and removable storage units 1818 and 1822 may communicate with one another over communication infrastructure 1802, which is commonly known as a "bus". Communications interface 1824 may communicate over any wired or wireless medium that allows for communication with other wired or wireless devices over network 1840. Network 1840 may communicate with Internet 1860 and/or database or databases 1850. Database 1850 may be utilized to implement any database described herein.

All claims herein only invoke 35 U.S.C. 112(f) when "means for" terminology is used, otherwise all claims herein recite the structure, material or acts that perform a function so claimed.

While the invention herein disclosed has been described by means of specific embodiments and applications thereof, numerous modifications and variations could be made thereto by those skilled in the art without departing from the scope of the invention set forth in the claims.

What is claimed is:

1. A urine testing system with nutritional recommendations, comprising:
   a test card configured to be exposed to a urine sample from a person, wherein the test card comprises
      a plurality of test regions, wherein each test region comprises one or more reagents configured to
         react with one or more substances present in the urine sample to which each test region is exposed; and
         change appearance of each test region based on a presence of or a quantity of the one or more substances in the urine sample;
   a test analyzer comprising a stored program configured to execute on one or more processors, wherein the stored program is configured to
      receive an image of the test card captured after the test card is exposed to the urine sample;
      analyze the image of the test card to generate a color adjustment that transforms colors in the image to adjusted colors;
      apply the color adjustment to the appearance of said each test region in the image to generate an adjusted appearance of each test region;
      determine an elapsed time between exposure of the test card to the urine sample and capture of the image;
      for each test region, calculate the presence of or the quantity of the one or more substances in the urine sample based on
         the adjusted appearance of each test region; and,
         the elapsed time between exposure of the test card to the urine sample and capture of the image; and,
   a computer configured to
      for at least one substance of the one or more substances,
         obtain a suggested range for a urine level of the at least one substance for the person;
         calculate a recommended consumption by the person of the at least one substance based on
            the suggested range; and,
            the quantity of the at least one substance in the urine sample;
   wherein the stored program is further configured to
      analyze the image of the test card to determine whether the image includes shadows;
      when the image includes shadows, generate an indication that the image is not usable.

2. The system of claim 1, wherein the quantity of the one or more substances in the urine sample is selected from a discrete set of quantity range values.

3. The system of claim 2, wherein the recommended consumption by the person of the at least one substance is selected from a discrete set of consumption values.

4. The system of claim 1, wherein the calculate the recommended consumption by the person of the at least one substance is further based on
   one or more characteristics of the person.

5. The system of claim 4, wherein the one or more characteristics of the person comprise one or more of gender, weight, height, body mass index, age, pregnancy status, allergies, medications, medical conditions, ethnicity, genome, microbiome, dietary restrictions, lifestyle, activity level, mental health, personal goals.

6. The system of claim 1, wherein the suggested range for the urine level of the at least one substance for the person is based on
   one or more characteristics of the person.

7. The system of claim 6, wherein the one or more characteristics of the person comprise one or more of gender, weight, height, body mass index, age, pregnancy status, allergies, medications, medical conditions, ethnicity, genome, microbiome, dietary restrictions, lifestyle, activity level, mental health, personal goals.

8. The system of claim 1, wherein the calculate the recommended consumption by the person of the at least one substance comprises
   calculate a recommended food consumption of the at least one substance; and,
   calculate a recommended supplement consumption of the at least one substance.

9. The system of claim 8, wherein
   the calculate the recommended food consumption of the at least one substance is based on the suggested range;
      the quantity of the at least one substance in the urine sample; and
      a food multiplier factor for the at least one substance, wherein the food multiplier factor is based on an effectiveness of the person obtaining the at least one substance from food; and,
   the calculate the recommended supplement consumption of the at least one substance is based on the suggested range;
      the quantity of the at least one substance in the urine sample; and
      a supplement multiplier factor for the at least one substance, wherein the supplement multiplier factor is based on an effectiveness of the person obtaining the at least one substance from supplements.

10. The system of claim 9, wherein the computer is further configured to
   obtain a substance level score based on a comparison of the quantity of the at least one substance in the urine sample to the suggested range, wherein said substance level score is 100% when the quantity of the at least one substance in the urine sample is within the suggested range;
   obtain a recommended daily allowance of the at least one substance for the person;
   calculate the recommended food consumption of the at least one substance based on
      the substance level score;
      the recommended daily allowance of the at least one substance for the person; and
      the food multiplier factor; and,
   calculate the recommended supplement consumption of the at least one substance based on
      the substance level score;
      the recommended daily allowance of the at least one substance for the person; and
      the supplement multiplier factor.

11. The system of claim 10, wherein the computer is further configured to
calculate a substance level deviation score as 100% less the substance level score;
calculate the recommended food consumption of the at least one substance as the recommended daily allowance of the at least one substance for the person, plus a product of
the substance level deviation score;
the recommended daily allowance of the at least one substance for the person; and
the food multiplier factor; and,
calculate the recommended supplement consumption of the at least one substance as a product of
the substance level deviation score;
the recommended daily allowance of the at least one substance for the person; and
the supplement multiplier factor.

12. The system of claim 10, wherein the computer is further configured to obtain one or more characteristics of the person;
calculate the recommended food consumption of the at least one substance based further on the one or more characteristics of the person; and,
calculate the recommended supplement consumption of the at least one substance based further on the one or more characteristics of the person.

13. The system of claim 12, wherein the one or more characteristics of the person comprise one or more of gender, weight, height, body mass index, age, pregnancy status, allergies, medications, medical conditions, ethnicity, genome, microbiome, dietary restrictions, lifestyle, activity level, mental health, personal goals.

14. The system of claim 8, wherein the computer is further configured to
determine one or more recommended foods and a quantity of the one or more recommended foods, wherein the quantity of the one or more recommended foods contains the recommended food consumption of the at least one substance.

15. The system of claim 14, wherein the determine one or more recommended foods and the quantity of the one or more recommended foods is based on
the recommended food consumption of the at least one substance; and,
one or more dietary preferences or restrictions of the person.

16. The system of claim 1, wherein
the test analyzer is further configured to calculate a hydration level; and,
the computer is further configured to calculate a recommended consumption of fluids or electrolytes based on the hydration level.

17. The system of claim 1, wherein the computer is further configured to calculate a recommended lifestyle change based on the quantity of the at least one substance in the urine sample.

18. The system of claim 17, wherein the recommended lifestyle change comprises a change in a level of activity.

19. The system of claim 17, wherein
the at least one substance in the urine sample comprises cortisol; and,
the recommended lifestyle change comprises adding a number of minutes of an activity, wherein the number of minutes is based on the quantity of cortisol in the urine sample.

20. The system of claim 1, wherein
the test card further comprises a plurality of fiducial markers, each fiducial marker of the plurality of fiducial markers comprising a reference color that is measured under a reference lighting condition; and
the stored program is further configured to
analyze the image of the test card to extract an appearance of each fiducial marker in the image; and,
analyze the appearance of each fiducial marker in the image to generate the color adjustment.

21. The system of claim 20, wherein the plurality of fiducial markers comprises
corner fiducial markers located at corners of a region of the test card that contains the plurality of test regions.

22. The system of claim 21, wherein the plurality of fiducial markers further comprises
a plurality of color fiducial markers.

23. The system of claim 22, wherein
the color adjustment comprises a function of the colors in the image of a region and of a position in the test card of the region;
the stored program is further configured to calculate the color adjustment as a linear regression with
inputs comprising positions and appearance in the image of the corner fiducial markers and of the plurality of color fiducial markers; and,
outputs comprising reference colors of the corner fiducial markers and of the plurality of color fiducial markers.

24. The system of claim 1, wherein the stored program is further configured to analyze the image of the test card to determine whether the image includes excessive glare;
when the image includes excessive glare, generate an indication that the image is not usable.

25. The system of claim 24, wherein analyze the image of the test card to determine whether the image includes excessive glare comprises
calculate a first color value of a first area of the image;
calculate a second color value of a second area of the image proximal to the first area; wherein a first reference color value of the first area under a reference lighting condition is similar to a second reference color value of the second area under the reference lighting condition;
determine whether a difference between the first color value and the second color area exceeds a threshold value.

26. The system of claim 1, wherein
the test card further comprises corner fiducial markers located at corners of a region of the test card that contains the plurality of test regions; and
analyze the image of the test card to determine whether the image includes shadows comprises
calculate color values of the corner fiducial markers; and,
determine whether differences among the color values of the corner fiducial markers exceed a threshold value.

27. A urine testing system with nutritional recommendations, comprising:
a test card configured to be exposed to a urine sample from a person, wherein the test card comprises
a plurality of test regions, wherein each test region comprises one or more reagents configured to
react with one or more substances present in the urine sample to which each test region is exposed; and change appearance based on a presence of or a quantity of the one or more substances in the urine sample;
at least one time indicator configured to change appearance based on a duration of time that the at least one time indicator is exposed to the urine sample;
a plurality of fiducial markers, each fiducial marker of the plurality of fiducial markers comprising a reference color that is measured under a reference lighting condition;
a test analyzer comprising a stored program configured to execute on one or more processors, wherein the stored program is configured to
receive an image of the test card captured after the test card is exposed to the urine sample;
analyze the image of the test card to extract
an appearance of each fiducial marker in the image;
an appearance of each test region in the image; and
an appearance of the at least one time indicator in the image;
analyze the appearance of each fiducial marker in the image to generate a color adjustment that transforms colors in the image to adjusted colors under the reference lighting condition;
apply the color adjustment to the appearance of each test region in the image to generate an adjusted appearance of each test region;
apply the color adjustment to the appearance of the at least one time indicator in the image to generate an adjusted appearance of the at least one time indicator;
analyze the adjusted appearance of the at least one time indicator to determine an elapsed time between exposure of the test card to the urine sample and capture of the image;
for each test region, generate a test result through calculation of the presence of or the quantity of the one or more substances in the urine sample based on
the adjusted appearance of each test region; and,
the elapsed time between exposure of the test card to the urine sample and capture of the image; and,
a computer configured to
for at least one substance of the one or more substances, obtain a suggested range for a urine level of the at least one substance for the person;
calculate a recommended consumption by the person of the at least one substance based on
the suggested range; and,
the quantity of the at least one substance in the urine sample.

28. The system of claim 27, wherein
the at least one time indicator comprises two or more time indicators;
the stored program is further configured to
analyze the adjusted appearance of each time indicator of the two or more time indicators to determine an elapsed time associated with each time indicator between exposure of each time indicator to the urine sample and capture of the image;
when the elapsed time associated with each time indicator differs from the elapsed time associated with a different time indicator by more than a threshold amount, generate an indication that test results are not valid.

29. A urine testing system with nutritional recommendations, comprising:
a test card configured to be exposed to a urine sample from a person, wherein the test card comprises
a plurality of test regions, wherein each test region comprises one or more reagents configured to
react with one or more substances present in the urine sample to which each test region is exposed; and
change appearance of each test region based on a presence of or a quantity of the one or more substances in the urine sample;
a test analyzer comprising a stored program configured to execute on one or more processors, wherein the stored program is configured to
receive an image of the test card captured after the test card is exposed to the urine sample;
analyze the image of the test card to generate a color adjustment that transforms colors in the image to adjusted colors;
apply the color adjustment to the appearance of said each test region in the image to generate an adjusted appearance of each test region;
determine an elapsed time between exposure of the test card to the urine sample and capture of the image;
for each test region, calculate the presence of or the quantity of the one or more substances in the urine sample based on
the adjusted appearance of each test region; and,
the elapsed time between exposure of the test card to the urine sample and capture of the image; and,
a computer configured to
for at least one substance of the one or more substances, obtain a suggested range for a urine level of the at least one substance for the person;
calculate a recommended consumption by the person of the at least one substance based on
the suggested range; and,
the quantity of the at least one substance in the urine sample;
wherein the calculate the recommended consumption by the person of the at least one substance comprises
calculate a recommended food consumption of the at least one substance; and,
calculate a recommended supplement consumption of the at least one substance;
wherein the calculate the recommended food consumption of the at least one substance is based on
the suggested range;
the quantity of the at least one substance in the urine sample; and
a food multiplier factor for the at least one substance, wherein the food multiplier factor is based on an effectiveness of the person obtaining the at least one substance from food; and,
wherein the calculate the recommended supplement consumption of the at least one substance is based on
the suggested range;
the quantity of the at least one substance in the urine sample; and
a supplement multiplier factor for the at least one substance, wherein the supplement multiplier factor is based on an effectiveness of the person obtaining the at least one substance from supplements.

30. A urine testing system with nutritional recommendations, comprising:
- a test card configured to be exposed to a urine sample from a person, wherein the test card comprises
  - a plurality of test regions, wherein each test region comprises one or more reagents configured to
    - react with one or more substances present in the urine sample to which each test region is exposed; and
    - change appearance of each test region based on a presence of or a quantity of the one or more substances in the urine sample;
- a test analyzer comprising a stored program configured to execute on one or more processors, wherein the stored program is configured to
  - receive an image of the test card captured after the test card is exposed to the urine sample;
  - analyze the image of the test card to generate a color adjustment that transforms colors in the image to adjusted colors;
  - apply the color adjustment to the appearance of said each test region in the image to generate an adjusted appearance of each test region;
  - determine an elapsed time between exposure of the test card to the urine sample and capture of the image;
  - for each test region, calculate the presence of or the quantity of the one or more substances in the urine sample based on
    - the adjusted appearance of each test region; and,
    - the elapsed time between exposure of the test card to the urine sample and capture of the image; and,
- a computer configured to
  - for at least one substance of the one or more substances,
    - obtain a suggested range for a urine level of the at least one substance for the person;
  - calculate a recommended consumption by the person of the at least one substance based on
    - the suggested range; and,
    - the quantity of the at least one substance in the urine sample;
- wherein the stored program is further configured to
  - analyze the image of the test card to determine whether the image includes excessive glare;
  - when the image includes excessive glare, generate an indication that the image is not usable; and,
- wherein analyze the image of the test card to determine whether the image includes excessive glare comprises
  - calculate a first color value of a first area of the image;
  - calculate a second color value of a second area of the image proximal to the first area,
    - wherein a first reference color value of the first area under a reference lighting condition is similar to a second reference color value of the second area under the reference lighting condition;
  - determine whether a difference between the first color value and the second color area exceeds a threshold value.

* * * * *